United States Patent
Reddy et al.

(10) Patent No.: US 10,786,679 B2
(45) Date of Patent: Sep. 29, 2020

(54) LEAD WITH INTEGRATED ELECTRODES

(71) Applicant: CARDIAC PACEMAKERS, INC., St. Paul, MN (US)

(72) Inventors: G. Shantanu Reddy, Minneapolis, MN (US); Andrew L. De Kock, Ham Lake, MN (US); Peter Hall, Andover, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 296 days.

(21) Appl. No.: 15/846,060

(22) Filed: Dec. 18, 2017

(65) Prior Publication Data
US 2018/0169425 A1    Jun. 21, 2018

Related U.S. Application Data

(60) Provisional application No. 62/437,064, filed on Dec. 21, 2016.

(51) Int. Cl.
*A61N 1/05* (2006.01)
*A61N 1/375* (2006.01)
*A61N 1/37* (2006.01)
*A61N 1/362* (2006.01)

(52) U.S. Cl.
CPC ....... *A61N 1/37512* (2017.08); *A61N 1/0565* (2013.01); *A61N 1/362* (2013.01); *A61N 1/3708* (2013.01)

(58) Field of Classification Search
CPC ..... A61N 1/0563; A61N 1/056; A61N 1/0565
See application file for complete search history.

(56) References Cited

U.S. PATENT DOCUMENTS

| 4,291,707 A | 9/1981 | Heilman et al. |
| 5,203,348 A | 4/1993 | Dahl et al. |
| 5,331,966 A | 7/1994 | Bennett et al. |
| 5,342,414 A * | 8/1994 | Mehra ............ A61N 1/0563 607/127 |
| 5,534,022 A | 7/1996 | Hoffmann et al. |
| 5,865,728 A | 2/1999 | Moll et al. |
| 6,038,483 A | 3/2000 | Kenknight et al. |
| 6,148,230 A | 11/2000 | Kenknight |
| 6,647,292 B1 | 11/2003 | Bardy et al. |

(Continued)

FOREIGN PATENT DOCUMENTS

| WO | 0241946 A2 | 5/2002 |
| WO | 2016148928 A1 | 9/2016 |
| WO | 2016149262 A1 | 9/2016 |

OTHER PUBLICATIONS

Moeinipour et al., "A Rare Central Venous Catheter Malposition: A Case Report," Anesth Pain Med., 4(1): 1-3, Feb. 5, 2014.

(Continued)

*Primary Examiner* — George R Evanisko
(74) *Attorney, Agent, or Firm* — Seager, Tufte & Wickhem LLP

(57) ABSTRACT

A lead for use with cardiac stimulus device with at least two electrodes positioned at a single longitudinal location is provided. The electrodes may include a shocking coil electrode and a sensing and/or pacing ring electrode and may be separated by an insulating element. The at least two electrically insulated electrodes may be electrically isolated and serve separate purposes in the device.

19 Claims, 26 Drawing Sheets

(56) References Cited

U.S. PATENT DOCUMENTS

| | | | |
|---|---|---|---|
| 6,721,597 | B1 | 4/2004 | Bardy et al. |
| 7,070,576 | B2 | 7/2006 | O'Brien et al. |
| 7,149,575 | B2 | 12/2006 | Ostroff et al. |
| 7,288,096 | B2 | 10/2007 | Chin |
| 7,299,092 | B2 | 11/2007 | Bardy et al. |
| 7,499,758 | B2 | 3/2009 | Cates et al. |
| 7,522,959 | B2 | 4/2009 | Hauser et al. |
| 7,570,997 | B2 | 8/2009 | Lovett et al. |
| 7,632,288 | B2 | 12/2009 | Wu |
| 7,655,014 | B2 | 2/2010 | Ko et al. |
| 7,657,322 | B2 | 2/2010 | Bardy et al. |
| 7,684,864 | B2 | 3/2010 | Olson et al. |
| 7,734,343 | B2 | 6/2010 | Ransbury et al. |
| 7,758,604 | B2 | 7/2010 | Wu et al. |
| 7,769,472 | B2 | 8/2010 | Gerber |
| 7,783,340 | B2 | 8/2010 | Sanghera et al. |
| 7,818,068 | B2 | 10/2010 | Meadows et al. |
| 7,890,191 | B2 | 2/2011 | Rutten et al. |
| 7,962,222 | B2 | 6/2011 | He et al. |
| 7,976,557 | B2 | 7/2011 | Kunis |
| 8,005,543 | B2 | 8/2011 | Libbus et al. |
| 8,050,774 | B2 | 11/2011 | Kveen et al. |
| 8,079,959 | B2 | 12/2011 | Sanghera et al. |
| 8,157,813 | B2 | 4/2012 | Ko et al. |
| 8,231,637 | B2 | 7/2012 | Greenberg et al. |
| 8,241,210 | B2 | 8/2012 | Lunsford et al. |
| 8,285,375 | B2 | 10/2012 | Bardy et al. |
| 8,364,280 | B2 | 1/2013 | Marnfeldt et al. |
| 8,386,048 | B2 | 2/2013 | McClure et al. |
| 8,483,841 | B2 | 7/2013 | Sanghera et al. |
| 8,483,843 | B2 | 7/2013 | Sanghera et al. |
| 8,491,615 | B2 | 7/2013 | Manderfeld et al. |
| 8,543,216 | B2 | 9/2013 | Carbunaru et al. |
| 8,577,454 | B2 | 11/2013 | Bardy et al. |
| 8,644,926 | B2 | 2/2014 | Ostroff et al. |
| 8,660,668 | B2 | 2/2014 | Bardy et al. |
| 8,706,217 | B2 | 4/2014 | Bardy et al. |
| 8,718,760 | B2 | 5/2014 | Bardy et al. |
| 8,718,793 | B2 | 5/2014 | O'Connor |
| 8,801,729 | B2 | 8/2014 | Ko et al. |
| 8,986,335 | B2 | 3/2015 | Chin |
| 9,079,035 | B2 | 7/2015 | Sanghera et al. |
| 9,216,280 | B1 | 12/2015 | Hakki et al. |
| 9,216,284 | B2 | 12/2015 | O'Connor |
| 2001/0044646 | A1 | 11/2001 | Marshall et al. |
| 2005/0043765 | A1 | 2/2005 | Williams et al. |
| 2008/0255647 | A1 | 10/2008 | Jensen et al. |
| 2009/0287285 | A1 | 11/2009 | Lynn |
| 2010/0269338 | A1 | 10/2010 | Dye |
| 2010/0292744 | A1* | 11/2010 | Hill ............ A61N 1/0565 607/2 |
| 2011/0072659 | A1 | 3/2011 | Swanson et al. |
| 2011/0093054 | A1* | 4/2011 | Ameri ............ A61N 1/0563 607/122 |
| 2012/0029335 | A1 | 2/2012 | Sudam et al. |
| 2012/0203321 | A1 | 8/2012 | Moffitt et al. |
| 2013/0166007 | A1 | 6/2013 | True et al. |
| 2014/0330326 | A1 | 11/2014 | Thompson-Nauman et al. |
| 2015/0025612 | A1 | 1/2015 | Haasl et al. |
| 2015/0045864 | A1 | 2/2015 | Howard |
| 2015/0051610 | A1 | 2/2015 | Schmidt et al. |
| 2015/0157851 | A1 | 6/2015 | Sefkow et al. |
| 2015/0196756 | A1 | 7/2015 | Stahmann et al. |
| 2015/0196757 | A1 | 7/2015 | Stahmann et al. |
| 2015/0196758 | A1 | 7/2015 | Stahmann et al. |
| 2015/0196769 | A1 | 7/2015 | Stahmann et al. |
| 2015/0224320 | A1 | 8/2015 | Stahmann |
| 2015/0297902 | A1 | 10/2015 | Stahmann et al. |
| 2015/0360036 | A1 | 12/2015 | Kane et al. |
| 2016/0038742 | A1 | 2/2016 | Stahmann et al. |
| 2016/0059007 | A1 | 3/2016 | Koop |
| 2016/0059022 | A1 | 3/2016 | Stahmann et al. |
| 2016/0059024 | A1 | 3/2016 | Stahmann et al. |
| 2016/0059025 | A1 | 3/2016 | Stahmann et al. |
| 2016/0089539 | A1 | 3/2016 | Gilkerson et al. |
| 2016/0213270 | A1 | 7/2016 | Cao et al. |
| 2016/0228712 | A1 | 8/2016 | Koop |
| 2016/0256692 | A1 | 9/2016 | Baru |
| 2016/0310746 | A1 | 10/2016 | Greenhut et al. |
| 2017/0020551 | A1 | 1/2017 | Reddy et al. |
| 2017/0021159 | A1 | 1/2017 | Reddy et al. |
| 2018/0036527 | A1 | 2/2018 | Reddy et al. |
| 2018/0036547 | A1 | 2/2018 | Reddy |
| 2018/0133462 | A1 | 5/2018 | Reddy |
| 2018/0133463 | A1 | 5/2018 | Reddy |
| 2018/0133494 | A1 | 5/2018 | Reddy |
| 2018/0169384 | A1 | 6/2018 | Reddy et al. |
| 2018/0169425 | A1 | 6/2018 | Reddy et al. |
| 2018/0178018 | A1 | 6/2018 | Reddy et al. |
| 2018/0178019 | A1 | 6/2018 | Reddy et al. |
| 2018/0193060 | A1 | 7/2018 | Reddy et al. |
| 2018/0214686 | A1 | 8/2018 | De Kock et al. |
| 2018/0256890 | A1 | 9/2018 | Fuhs et al. |
| 2018/0264270 | A1 | 9/2018 | Koop et al. |
| 2018/0296824 | A1 | 10/2018 | De Krock et al. |
| 2018/0325480 | A1 | 11/2018 | Liu et al. |
| 2018/0344200 | A1 | 11/2018 | Thakur et al. |
| 2018/0344252 | A1 | 11/2018 | An et al. |

OTHER PUBLICATIONS

Schuder et al., "Experimental Ventricular Defibrillation with an Automatic and Completely Implanted System," Trans. Amer. Soc. Artif. Int. Organs, XVI: 207-212, 1970.

Schuder et al., "The Role of an Engineering Oriented Medical Research Group in Developing Improved Methods and Devices for Achieving Ventricular Defibrillation: The University of Missouri Experience," Pace, 16: 95-124, Jan. 1993.

Ghosh et al., "A Rare Malposition of the Thoracic Venous Catheter Introduced via the Left Internal Jugular Vein," Indian J. Crit. Care Med., 12(4): 201-203, Oct.-Dec. 2008.

Loukas et al., "The Clinical Anatomy of the Internal Thoracic Veins," Folia Morphol, 66(1): 25-32, 2007.

Advisory Action Before the Filing of an Appeal Brief for U.S. Appl. No. 15/667,167, dated Mar. 21, 2019.

Final Office Action for U.S. Appl. No. 15/667,167, dated Jan. 10, 2019.

Non-Final Office Action for U.S. Appl. No. 15/667,167, dated Jun. 26, 2018.

Non-Final Office Action for U.S. Appl. No. 15/667,167, dated Aug. 7, 2019.

Final Office Action for U.S. Appl. No. 15/667,221, dated Apr. 11, 2019.

Non-Final Office Action for U.S. Appl. No. 15/667,221, dated Oct. 1, 2018.

Notice of Allowance and Fees Due for U.S. Appl. No. 15/667,221, dated Jul. 11, 2019.

Amendment for U.S. Appl. No. 15/667,167, dated Sep. 17, 2018.

Amendment for U.S. Appl. No. 15/667,167, dated Oct. 9, 2019.

Amendment After Final Office Action for U.S. Appl. No. 15/667,167, dated Mar. 11, 2019.

Request for Continued Examination (RCE) for U.S. Appl. No. 15/667,167, dated Apr. 10, 2019.

Amendment for U.S. Appl. No. 15/667,221, dated Dec. 21, 2018.

Amendment After Final Office Action for U.S. Appl. No. 15/667,221, dated May 22, 2019.

A Patient's Guide-Living with your S-ICD System, 2012.

Ferrari et al., Journal of Arrhythmia, 1-3, 2015.

Lieberman et al., MDT Anterior Posterior SubQ Testing Article, Heart Rhythm, vol. 5, No. 1, 28-34, 2008.

Jolley et al., Finite element modeling of subcutaneous implantable defibrillator electrodes in an adult torso, Heart Rhythm (2009).

Weiss et al., Arrhythmia/Electrophysiology, Circulation, 128, 944-954, 2013.

* cited by examiner

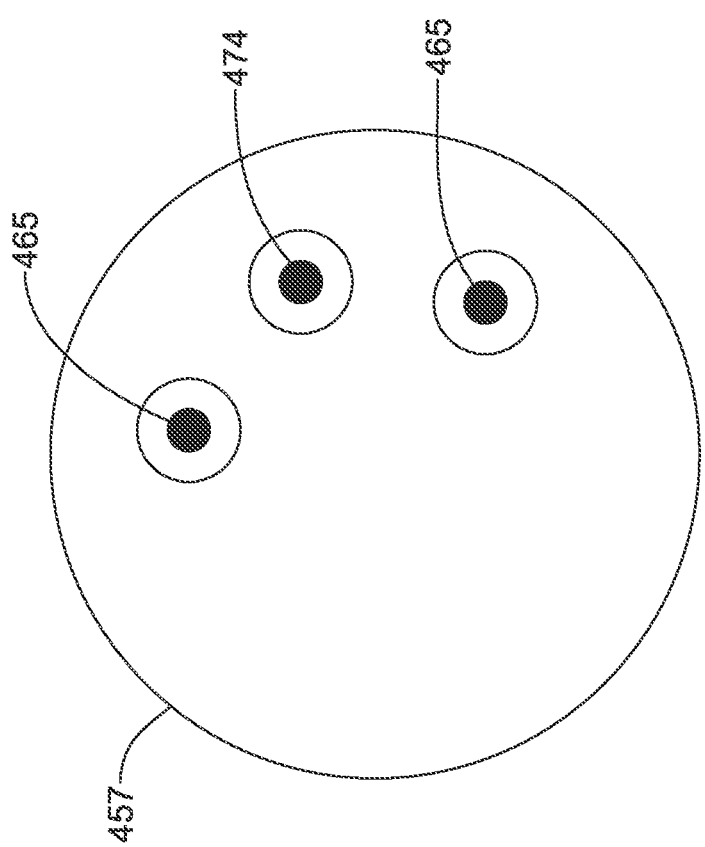

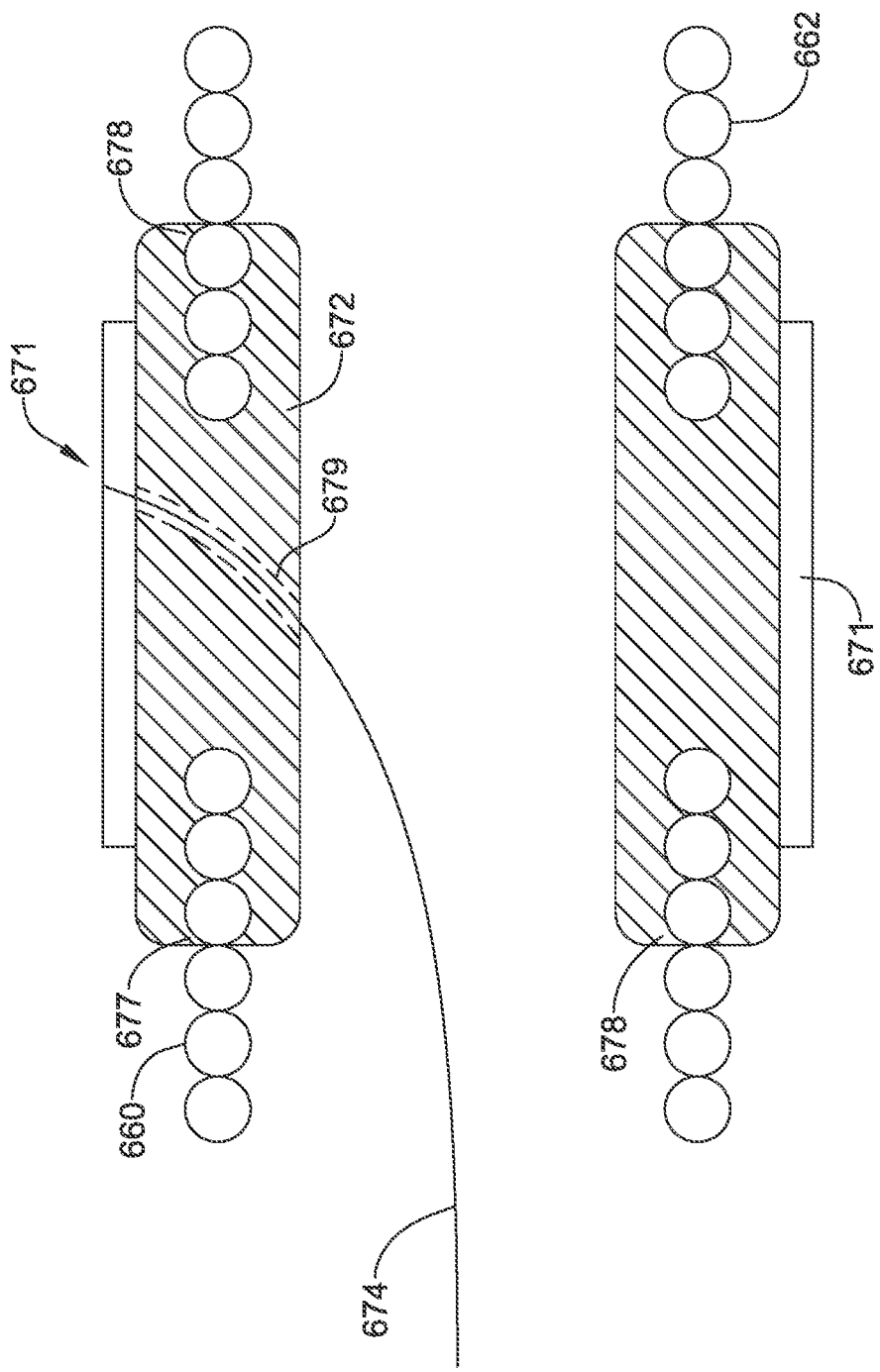

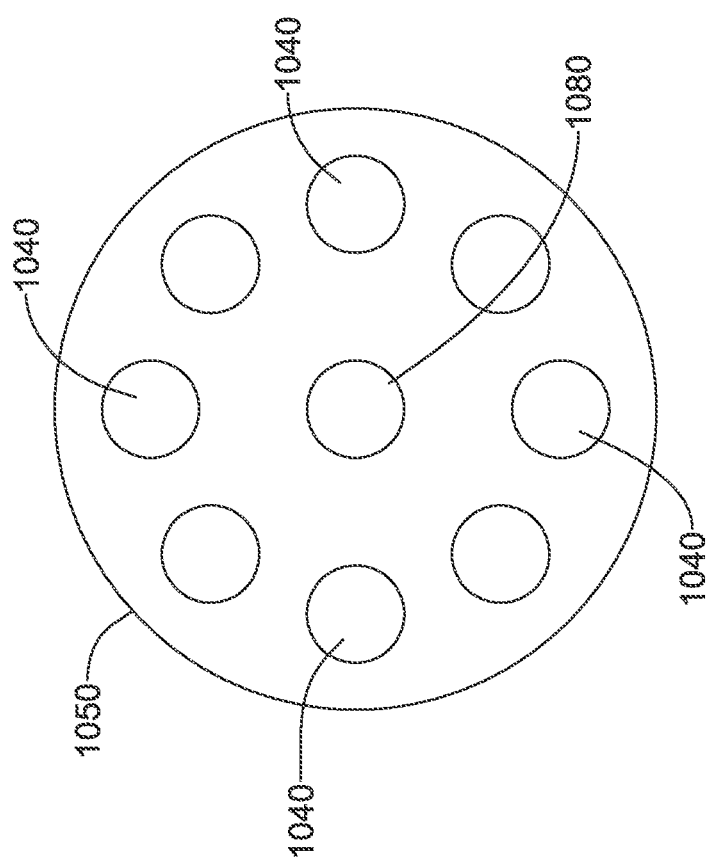

LEAD WITH INTEGRATED ELECTRODES

CROSS REFERENCE TO RELATED APPLICATIONS

The present application claims the benefit of and priority to U.S. Provisional Patent Application Ser. No. 62/437,064, filed Dec. 21, 2016, and titled LEAD WITH INTEGRATED ELECTRODES, the disclosure of which is incorporated herein by reference.

BACKGROUND

The implantable defibrillator has been demonstrated to extend patient lives by treatment of potentially deadly arrhythmias. Over time, various efforts have been made to address complications associated with implantation of such devices. For example, early devices generally used epicardial patch electrodes implanted via thoracotomy, with attendant surgical risks and significant risks of failure of the epicardial patch electrodes and associated leads. The use of transvenous leads represented a major advance, avoiding the thoracotomy and improving reliability. However, lead failure remained a significant issue, as the lead attachment in the heart cause the lead to flex with each heartbeat. The advent of subcutaneous defibrillators allows avoidance of these lead failure issues, with leads implanted beneath the skin and over the ribcage of the patient and not subjected to the repeated flexing.

However, subcutaneous defibrillators require higher energy for defibrillation, causing the pulse generators for such systems to be larger than their transvenous predecessors, and both bradycardia pacing and anti-tachycardia pacing to avoid high voltage shock for certain conditions, is of limited utility as such pacing subcutaneously can be very uncomfortable for the patient. This has led to interest in further alternative locations and configurations for implantable defibrillators, and other medical devices such as the implantable pacemaker.

OVERVIEW

The present inventors have recognized, among other things, that locating pacing and defibrillation electrodes in the same location on a lead designed for placement in the internal thoracic vasculature including, in particular, the internal thoracic vein (ITV), sometimes also referred to as the internal mammary vein, presents an opportunity for an improved implantable cardiac device.

A first non-limiting example takes the form of an implantable lead for use with an implantable cardiac stimulus device, the lead comprising a lead body having a longitudinal axis extending between a proximal end and a distal end, wherein the proximal end is adapted for coupling to the implantable cardiac stimulus device, and an electrode structure is disposed adjacent the distal end of the lead body, the electrode structure including at least first and second electrodes that are electrically isolated from one another, wherein at least a portion of the first electrode and at least a portion of the second electrode overlap one another at a longitudinal location on the lead.

Additionally or alternatively to the example above, in a second example, the first electrode is a coil electrode and the second electrode is a ring electrode.

Additionally or alternatively to the examples above, in a third example, the coil electrode is a high voltage shocking electrode and the ring electrode is a sensing and/or pacing electrode.

Additionally or alternatively to the examples above, in a fourth example, the at least first and second electrodes includes three to eight electrodes.

Additionally or alternatively to the examples above, in a fifth example, the implantable lead further comprises insulation disposed between the first and second electrodes.

Additionally or alternatively to the examples above, in a sixth example, the first electrode is a coil electrode and the second electrode is a ring electrode, and the insulation includes an insulating coating disposed on an inner surface of the ring electrode or on a portion of the coil electrode that contacts the ring electrode, or both.

Additionally or alternatively to the examples above, in a seventh example, the first electrode is a coil electrode and the second electrode is a ring electrode, and the insulation includes an insulating element disposed on an inner surface of the ring electrode, wherein the insulating element contacts the coil electrode to insulate the first electrode from the second electrode.

Additionally or alternatively to the examples above, in an eighth example, the coil electrode includes a gap between coil windings, the gap sized to allow connection of the ring electrode to a cable connector in the interior of the lead body.

Additionally or alternatively to the examples above, in a ninth example, the gap is defined by a region of coil windings having an increased pitch compared to coil regions distal and proximal of the ring electrode.

Additionally or alternatively to the examples above, in a tenth example, the region of coil windings having an increased pitch is disposed under the ring electrode.

Additionally or alternatively to the examples above, in a eleventh example, the first and second electrodes are separated radially by a space, wherein the insulation includes an insulating element that fills the space.

Additionally or alternatively to the examples above, in a twelfth example, the first electrode is a coil electrode an the second electrode is a ring electrode, wherein the coil electrode includes a preformed region extending longitudinally through the ring electrode, wherein the insulation is disposed between the preformed region of the coil and the ring electrode.

Additionally or alternatively to the examples above, in a thirteenth example, the lead body includes one or more recesses on an outer surface thereof, each recess configured to receive the preformed region of the coil electrode.

Additionally or alternatively to the examples above, in a fourteenth example, the insulating element includes a threaded inner surface configured to receive coil windings of the coil electrode.

Additionally or alternatively to the examples above, in a fifteenth example, the insulating element includes proximal and distal channels configured to receive a distal end of a first coil electrode and a proximal end of a second coil electrode.

Additionally or alternatively to the examples above, in a sixteenth example, the insulating element includes an aperture therethrough for receiving a cord connector for a ring electrode.

Additionally or alternatively to the examples above, in a seventeenth example, the implantable lead further comprises a distal terminal electrode.

Additionally or alternatively to the examples above, in a eighteenth example, the at least first and second electrodes include a coil electrode and two sensing/pacing electrodes, wherein two cable connectors attached to the two sensing/pacing electrodes extend proximally in a coradial coil through a first lumen in the lead, and a cable connector attached to the coil electrode extends proximally through a second lumen in the lead.

Additionally or alternatively, a nineteenth example takes the form of an implantable lead for use with an implantable cardiac stimulus device, the lead comprising a lead body having a longitudinal axis extending between a proximal end and a distal end, wherein the proximal end is adapted for coupling to the implantable cardiac stimulus device, an electrode structure disposed adjacent the distal end of the lead body, the electrode structure including at least one coil electrode and at least one ring electrode, wherein at least a portion of the coil electrode and at least a portion of the ring electrode overlap one another at a longitudinal location on the lead, and insulation disposed on an inner surface of the ring electrode or on a portion of the coil electrode that contacts the ring electrode, or both.

Additionally or alternatively, a twentieth example takes the form of an implantable cardiac stimulus system, comprising an implantable cardiac stimulus device, a lead body connectable to the implantable cardiac stimulus device, the lead body having a longitudinal axis extending between a proximal end and a distal end, wherein the proximal end is adapted for coupling to the implantable cardiac stimulus device, and an electrode structure disposed adjacent the distal end of the lead body, the electrode structure including at least first and second electrodes that are electrically isolated from one another, wherein at least a portion of the first electrode and at least a portion of the second electrode overlap one another at a longitudinal location on the lead.

Each of these non-limiting examples can stand on its own, or can be combined in various permutations or combinations with one or more of the other examples. This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 11B is a radial cross-sectional view taken along line 11B-11B of FIG. 11A;

FIG. 13B is a partial longitudinal cross-sectional view taken along line 13B-13B of FIG. 13A;

FIG. 17B is a radial cross-sectional view of another illustrative lead body.

DETAILED DESCRIPTION

Figure 1:
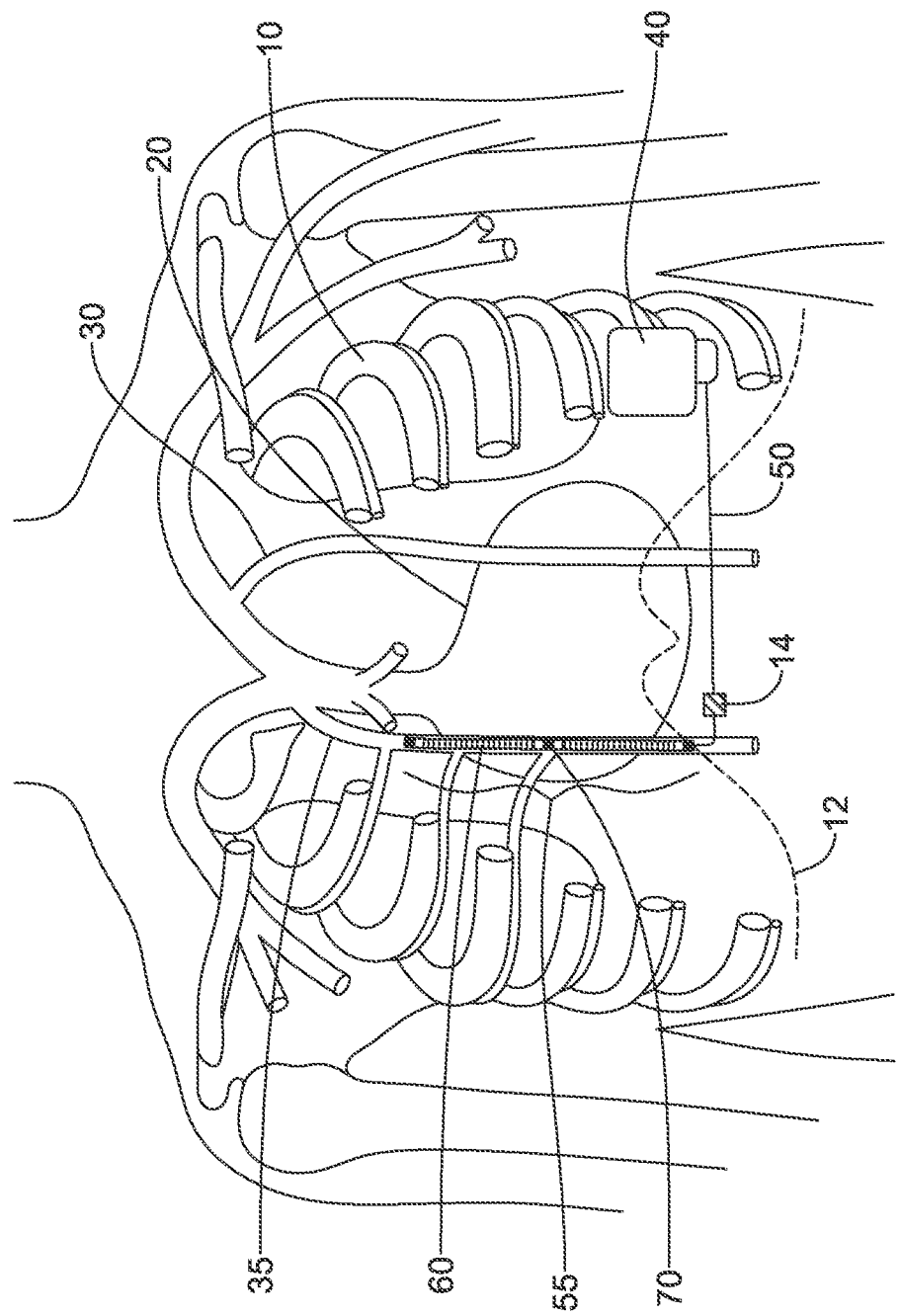
FIG. 1 illustrates implantation of a lead from an inferior position in the right internal thoracic vein (ITV)

The S-ICD System from Boston Scientific provides benefits to the patient including the preservation of transvenous anatomy and avoidance of intracardiac leads, which may fracture and/or may serve as conduits for infection to reach the heart, and can occlude blood vessels going into the heart, making later placement of leads or other devices in the heart more difficult. Some examples and discussion of subcutaneous lead implantation may be found in U.S. Pat. No. 8,157,813, titled APPARATUS AND METHOD FOR SUBCUTANEOUS ELECTRODE INSERTION, and US PG Publication No. 20120029335, titled SUBCUTANEOUS LEADS AND METHODS OF IMPLANT AND EXPLANT, the disclosures of which are incorporated herein by reference. Additional subcutaneous placements are discussed in U.S. Pat. No. 6,721,597, titled SUBCUTANEOUS ONLY IMPLANTABLE CARDIOVERTER DEFIBRILLATOR AND OPTIONAL PACER, and the above mentioned U.S. Pat. No. 7,149,575, the disclosures of which are incorporated herein by reference.

While many patients can be well treated with the S-ICD System, there continue to be limitations. Increased energy requirements of the S-ICD System, perceived difficulty with providing chronic bradycardia pacing, and unavailability of anti-tachycardia pacing to terminate select fast tachycardia, have created interest in alternative defibrillator and/or pacemaker placement techniques. One proposal has included a substernal placement, with a lead extending beneath the sternum from a position inferior to the lower rib margin, such as in US PG Patent Application Pub. No. 20170021159, titled SUBSTERNAL PLACEMENT OF A PACING OR DEFIBRILLATING ELECTRODE, the disclosure of which is incorporated herein by reference. Proposals for a substernal device have been referred to as extravascular, insofar as the lead does not enter or reside in the vasculature. Such devices are distinct from early generation epicardial devices in that the lead and electrode would not touch the heart or enter or be secured to the pericardium.

A further alternative placement involves inserting a lead into the internal thoracic vein (ITV), also referred to as the internal mammary vein, from a superior or inferior approach, such as in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference. The internal thoracic vein (ITV) is a vessel that drains the chest wall and breasts. There are both left and right internal thoracic veins on either side of the sternum, beneath the ribs. The ITV arises from the superior epigastric vein, accompanies the internal thoracic artery along its course and terminates in the brachiocephalic vein. The ITV may make a suitable location for placement of a cardiac stimulus lead, and the ITV may be accessed by first accessing the superior epigastric vein percutaneously or via cutdown in the paraxiphoid window or parasternally, for example through one of the intercostal spaces, as discussed in the 62/371,343 Provisional Patent Application. Additionally, the mediastinal space or the thoracic vasculature may provide a useful location for placement of the cardiac stimulus lead, either as directed accessed as in the Ser. No. 15/208,682 patent application, or if accessed by entry into and then exit from the ITV.

The cardiac pacing and defibrillation electrodes on the leads of the S-ICD System are generally located separately from each other, spaced apart longitudinally along the lead. For example, pacing and/or sensing electrodes are often positioned on either side of a defibrillation coil electrode. However, such placement may not achieve optimal defibrillation performance and optimal pacing/sensing performance. When the pacing and defibrillation electrodes are spaced apart longitudinally along the lead, the optimal location for the defibrillation electrode may result in the pacing electrodes being located in a less desirable location. Similarly, if the lead is placed such that the pacing electrodes are optimally located, the spacing between electrodes may result in the defibrillation electrode being located in a less optimal location. The distance between the heart and the subcutaneous or ITV location of the lead may make it difficult to place all of the pacing and defibrillation electrodes on a single lead at their optimal locations. The inventors have recognized that locating pacing and defibrillation electrodes such that at least a portion of the electrodes overlap, thereby placing portions of the electrodes at the same longitudinal location on the lead may be beneficial when the lead is located subcutaneously or in the ITV. Additionally, locating the pacing and shocking electrodes such that at least a portion of the electrodes overlap, thereby placing portions of the electrodes at the same longitudinal location on the lead may be desirable for a lead placed in the mediastinal space.

A design where a coil electrode has insulated ring electrodes located along the length of the coil electrode is described. The design may be made up of coil segments that could be connected together as a group, or which may be separately addressable. If desired, each individual ring or coil segment may be utilized as a pacing cathode or anode or, in the alternative, as a sensing electrode. If a high voltage shock is desirable, the coil segments and/or ring electrodes may be activated to deliver a shock, or alternatively one or more segments or ring electrodes may be inactive (such as set in a high impedance state or allowed to float, electrically speaking) during high voltage therapy delivery.

FIG. 1 illustrates portions of the thoracic anatomy including location of the left ITV 30 and the right ITV 35. The ribcage is shown at 10 and an outline of the heart is shown at 20. An implantable system having an implantable pulse generator 40 and lead 50 with distal electrode structure 55 is shown emplaced in the right ITV 35. As shown, the electrode structure 55 includes a continuous coil electrode 60 with three pacing/sensing electrodes 70 disposed over the coil electrode. The distal portion of the electrode structure may include a fixation apparatus or shape for the flexible lead, such as a 2 or 3 dimensional curve (see FIG. 18), tines (see FIG. 19), an expandable member (see FIGS. 20 and 22), or hooks or a side-extending engagement structure (see FIGS. 21 and 23) as described below. The sternum is not shown to allow visualization of the heart in relation to the ITVs 30, 35.

Parasternal access to the ITVs may be achieved at any location, such as superior or inferior positions. In some examples the ITV can be accessed from a position inferior to the ribcage. FIG. 1 shows implantation from an inferior position in an ITV. In this example, the right ITV 35 has been accessed by introduction through the superior epigastric vein from a location inferior to the rib margin 12 or, in the alternative, by introduction through the musculophrenic vein which runs along the lower rib margin (such access is described in detail in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference). An implantable device has been placed including a lead 50 having a distal electrode structure 55 and a canister 40, with the canister 40 placed at approximately the left axilla. The canister 40 may be placed as desired, for example at the anterior axillary line, the midaxillary line, or in the posterior axillary line.

In the illustration, a suture sleeve is shown at 14 and is used to fixate the lead 50, for example, to the subcutaneous fascia. For placement, the right ITV 35 may be accessed and a tunnel established between the left axilla and the access location such as along a portion of the inframammary crease. The lead 50 may, in this case, be relatively stiff to assist in keeping it emplaced in the patient as shown, if desired. In the example of FIG. 1, a left axillary canister location is shown; a right sided, pectoral or subclavicular left or right position may be used instead, in combination with the right ITV placement or, alternatively a left ITV placement.

The ITV may be accessed using standard access techniques known in the art for implanting traditional transvenous pacemakers and defibrillators. In any location, access may be achieved using ultrasound guided needle insertion. The access method may resemble the Seldinger technique, though in this case the muscle adjacent the sternum in the intercostal space would first be traversed. Other venipuncture or cutdown techniques may be used instead.

The Seldinger technique may include creating a puncture at the desired access location, with a hollow needle or trocar, for example under ultrasound guidance, introducing a guidewire through the needle and into the desired blood vessel, removing the needle, keeping the guidewire in place, and then inserting an introducer sheath, which may have a valve at its proximal end, over the guidewire. The introducer sheath may be advanced to a location to place its distal tip near the desired location of the distal end of the lead. Contrast injection may be useful to visualize the ITV structures. A guide catheter and guidewire may then be introduced through the introducer sheath. The guidewire may be the same as used in gaining initial access (if one is used to gain access), or may be a different guidewire. In another example, a cut-down technique may be used to access the desired ITV by incision through the skin. The incision may be made laterally from the location of the ITV. Next, possibly after visual confirmation the desired vessel is accessed, incision into the selected vein can be made, followed by insertion of the lead. Once access to a selected ITV is achieved, the vessel can be traversed in a superior or inferior direction to place the lead with the electrodes 60, 70 at the desired level by entering the corresponding ITV.

Some illustrative approaches for use of the ITV are shown in U.S. patent application Ser. No. 15/801,719, titled PARASTERNAL PLACEMENT OF AN ACTIVE MEDICAL DEVICE USING THE INTERNAL THORACIC VASCULATURE, the entire contents of which are herein incorporated by reference. Some examples herein use the ITV for implantation, while others may provide a fully subcutaneous system such as shown in U.S. Pat. Nos. 6,721,597, 7,149,575, and 8,157,813. In other examples, the leads shown herein may be used as subcutaneous leads for use with a device or system having epicardial or transvenous leads. Still other examples may implant the lead in the mediastinum in a generally substernal location.

The lead 50 may be tunneled from the parasternal access location across and down to the pulse generator 40, which may be implanted at the left axilla as illustrated. For ease of illustration the pulse generator 40 is shown at about the anterior axillary line, level with the cardiac apex and/or inframammary crease. In other examples the pulse generator 40 may be more lateral and/or posterior, such as at the mid-axillary line or posterior axillary line, or may even be more dorsal with placement dorsally between the anterior surface of the serratus and the posterior surface of the latissimus dorsi. A right sided axillary, pectoral or subclavicular left or right position may be used instead, in combination with right or left ITV placement.

In some examples, a flexible lead may be introduced with the support of a guide catheter during advancement. The guide catheter may receive the lead through a guide catheter lumen that serves to retain a fixation apparatus or shape for the flexible lead, such as a 2-dimensional or 3-dimensional curvature (see FIG. 18), tines (see FIG. 19), an expandable member (see FIGS. 20 and 22), or hooks or a side-extending engagement structure (see FIGS. 21 and 23). A stylet may be placed through the lead, or a portion thereof, to retain a straight shape during implantation; upon removal of the stylet, a curvature (see FIG. 18) may then be released for securing the lead in place.

In another alternative, the guide catheter and guidewire may be omitted by providing a lead with a flexible or steerable structure, and/or a lead configured for implantation using a steerable stylet. For example, a lead may be configured to be implanted using a steerable stylet in a lumen thereof, with the initial placement into the left ITV 30 (or right ITV 35, if desired) at the distal end of the introducer sheath, possibly using contrast visualization, if desired. Once initial access is achieved, simply pushing the stylet should be sufficient to implant the lead to a desired level in the ITV. The stylet may have a secondary function of preventing an anchoring structure of the lead from assuming an anchoring shape or releasing an anchoring tine, hook, expandable member, stent or other device. In other examples, a guidewire and/or sheath may not be needed. Due to the limited angulation required for accessing the ITV from a parasternal incision, the lead may be inserted directly into the ITV, reducing the time and complexity of the procedure.

The lead 50 shown in FIG. 1 includes a defibrillating coil electrode 60 and three ring electrodes 70 disposed longitudinally along the coil. The ring electrodes 70 may serve as sensing and/or pacing electrodes. The coil electrode 60 and pulse generator 40 may serve as therapy delivery electrodes.

Figure 2:
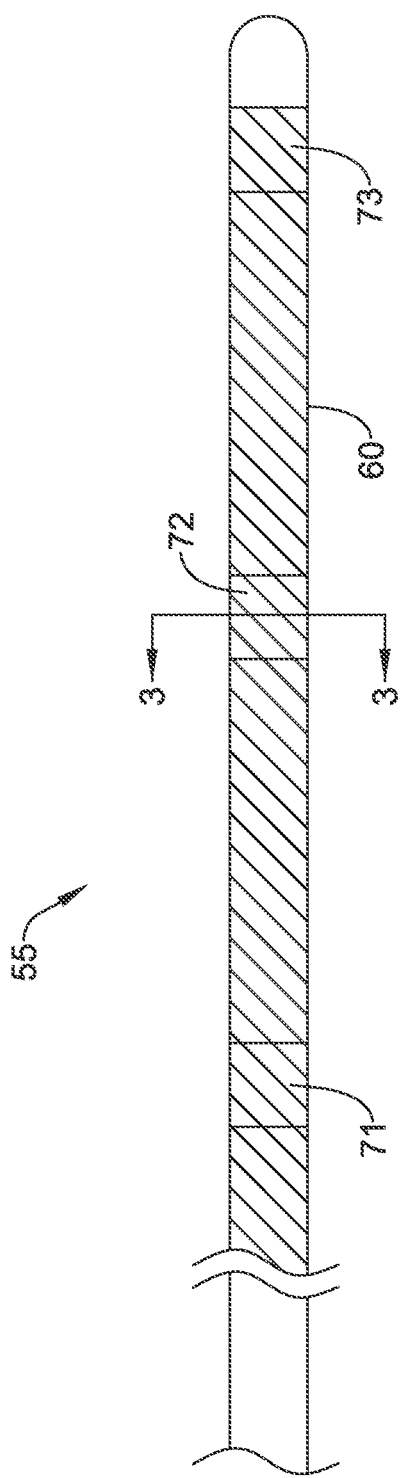
FIG. 2 shows the distal end of an illustrative lead that may be used in the implantation configuration of FIG. 1.

FIG. 2 illustrates the distal end of the lead shown in FIG. 1, with electrode structure 55. The three ring electrodes 70 include a proximal electrode 71, a middle electrode 72, and a distal electrode 73. The ring electrodes are spaced apart longitudinally from each other along the coil electrode 60, but the ring electrodes are positioned at substantially the same longitudinal location as a portion of the coil electrode 60. Overlapping the coil and ring electrodes at the same longitudinal location may be achieved with various internal structures.

Figure 3:
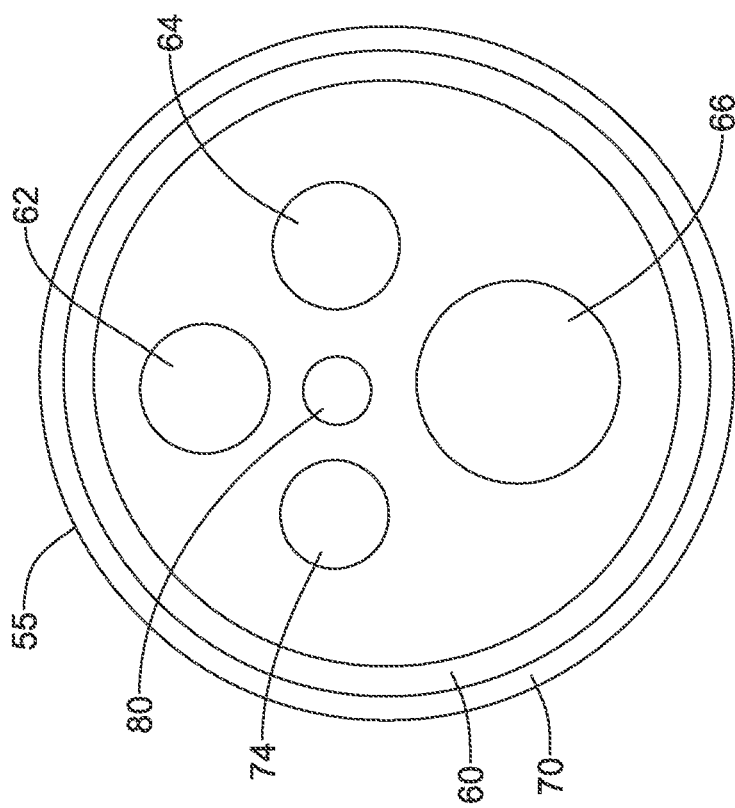
FIG. 3 is a cross-sectional view taken along line 3-3 of the lead of FIG. 2.

FIG. 3 is an illustrative cross-sectional view of the electrode structure shown in FIG. 2, taken through line 3-3. FIG. 3 illustrates a possible orientation of the cable conductors within the electrode structure 55. The pacing/sensing electrode ring electrodes 70 may be disposed over the coil electrode 60. The cable conductors for two of the pacing/sensing electrodes 70 may form a coradial coil 66 extending longitudinally within the electrode structure 55. One or more cable conductors 62, 64 for the defibrillation coil 60 may extend longitudinally within the electrode structure at a location spaced apart from the cable conductor coradial coil 66 for the pacing/sensing electrodes. The third ring electrode cable conductor 74 may be disposed spaced apart from the coradial coil 66 and the coil electrode cable conductors 62, 64. The electrode structure 55 may also include an internal lumen 80 for a guide wire or other delivery device.

In another alternative, the lumen 80 may be replaced with a central conductor that attaches to a distal tip electrode, on which the lead body may be co-extruded. Such a structure may be useful to provide extra pull strength to the structure in the event it must be extracted from a patient.

Figure 4:
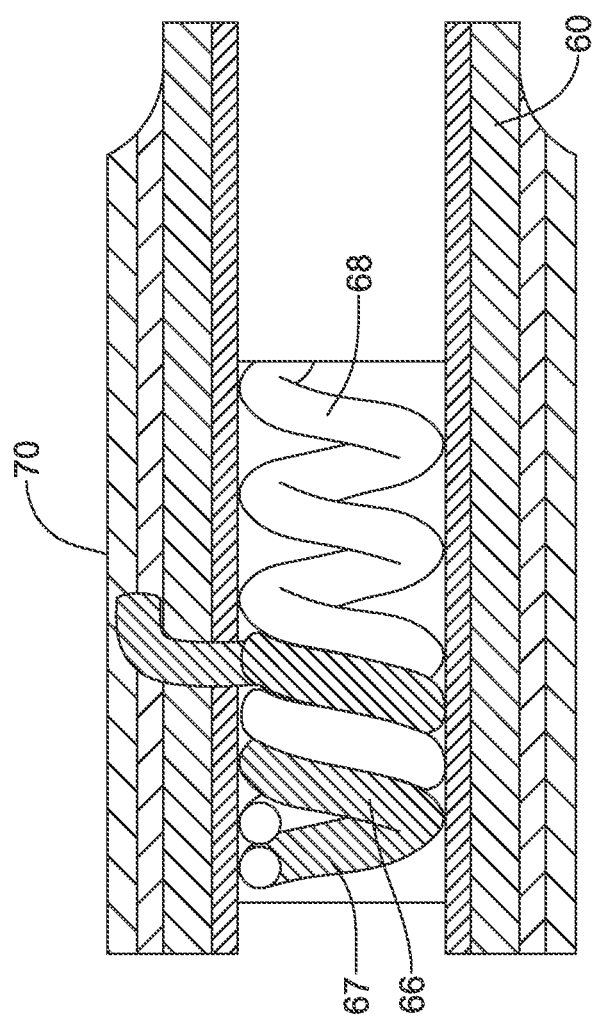
FIG. 4 is a longitudinal cross-sectional view of a portion of another illustrative electrode structure.

FIG. 4 is a longitudinal cross-sectional view of another electrode structure showing the coradial coil 66 made up of cable conductors 67, 68 coiled together. One end of coiled cable conductor 67 transitions from wound coil to a straight section to facilitate connection to the ring electrode 70 that extends circumferentially around the coil electrode 60. The other coiled cable conductor 68 continues and would be connected to another ring electrode located further along the electrode structure. While the example shown in FIG. 4 has two cable conductors forming a coradial coil, it will be understood that more wires may be included in the coradial coil, depending on the number of sensing/pacing electrodes present.

Figure 5:
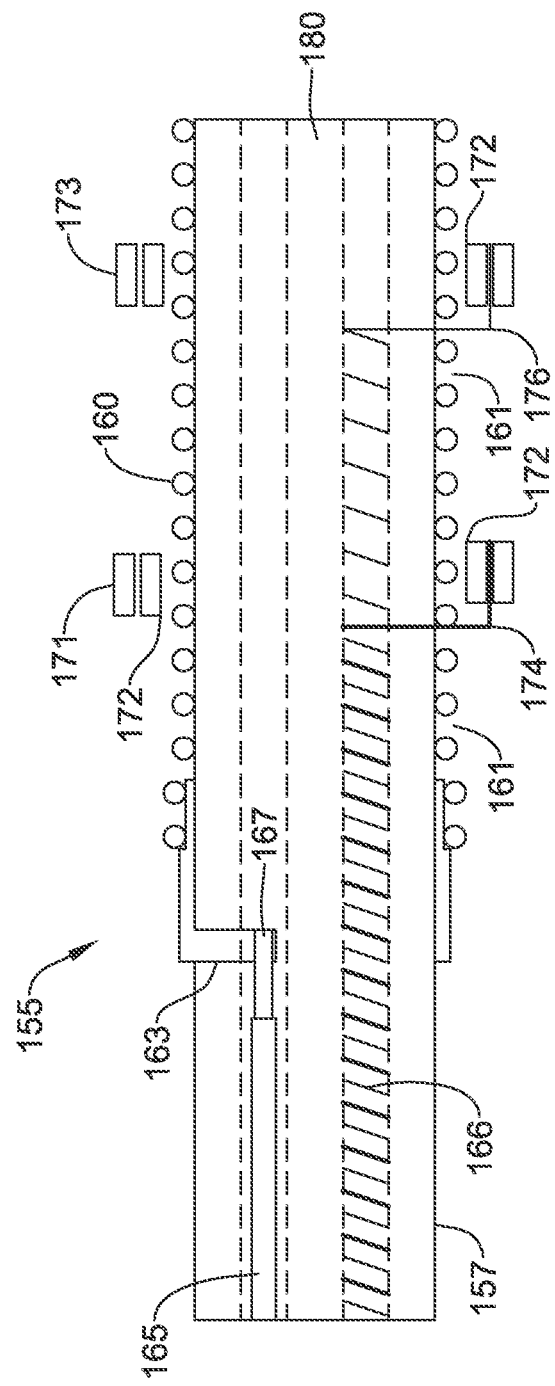
FIG. 5 is a longitudinal cross-sectional view of a portion of another illustrative electrode structure.

FIG. 5 is a longitudinal cross-sectional view of another electrode structure 155 including a coil defibrillation electrode 160 disposed over a lead body 157. First and second sensing/pacing ring electrodes 171, 173 are disposed circumferentially around the coil electrode 160 such that a portion of the coil electrode 160 is disposed between an insulating element 172 on each of the ring electrodes 171, 173 and the outer surface of the lead body 157. The insulating element 172 may include an ethylene tetrafluoroethylene (ETFE) coating, a polymer coating or separate element, or other suitable insulating material. The insulating element 172 allows the ring electrodes 171, 173 to be disposed at the same longitudinal position as a portion of the coil electrode 160. Each of the ring electrodes 171, 173 has a cable conductor 174, 176 that extends through a space 161 between windings of the coil electrode 160 and through the lead body 157.

The cable conductors 174, 176 may be laser welded to the associated ring electrode 171, 173. Inside the lead body 157, the cable conductors 174, 176 may form a coradial coil 166 as they extend to the proximal end of the lead. The ring electrodes 171, 173 may be swaged or welded to an inner support ring. The coradial coil 166 may include more than two cable conductors, such as three or four, or however many ring electrodes are desired. The coil electrode 160 is coupled to a coated cable 165 disposed within the tube via a coupling element 163. The coupling element 163 extends from the outer surface of the lead body 157 through an opening in the tube and into the interior of the tube. The coupling element 163 may be connected to a stripped cable portion 167. The electrode structure 155 may include an internal lumen 180 for receiving a guide wire or other delivery device. In another example, the insulating element may be a coating 272 on the coil electrode, as shown in FIG. 7.

It should be understood that connection of the high voltage cable 167 to the coil electrode 160 may include multiple, redundant connections to the high voltage cable 167 and/or a plurality of redundant high voltage cables. For example referring to FIG. 2, the coil 60 may be a single coil with ring electrodes 71, 72, 73 thereon, with the coil 60 having multiple connections to the high voltage conductor(s) inside the lead body such as at the proximal end of the coil and between the ring electrodes. Such redundant connection may aid in lead reliability and may also serve to enhance output field consistency along the length of the coil.

Figure 6:
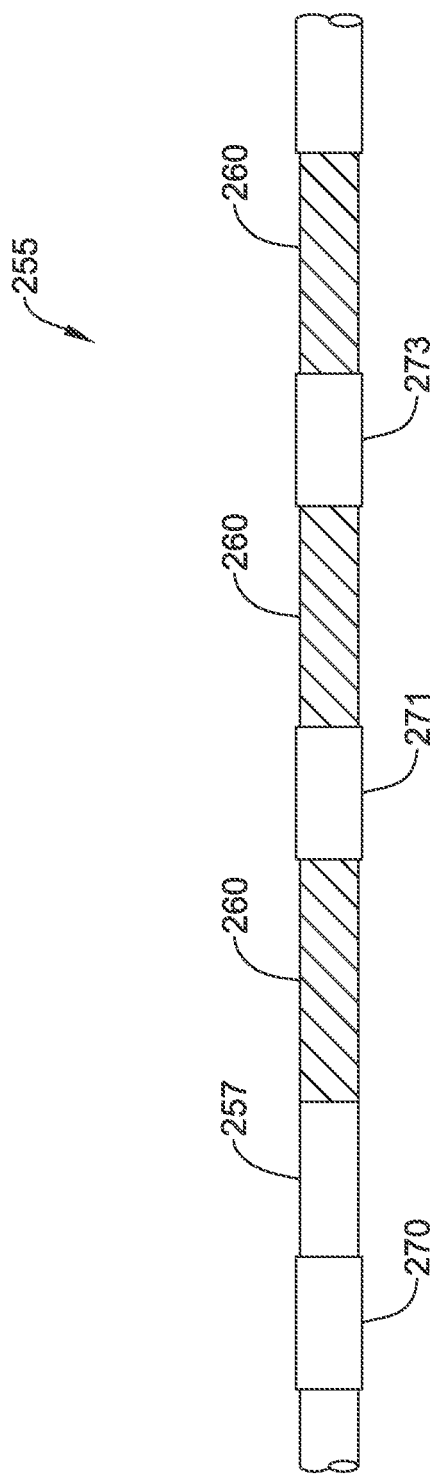
FIG. 6 is a side view of a portion of another illustrative electrode structure.

FIG. 6 is a side view of another example electrode structure 155, with three separate sensing/pacing electrodes 270, 271, 273 spaced apart longitudinally from one another. In this example, two of the sensing/pacing electrodes 271, 273 are disposed over a single continuous coil electrode 260, and one sensing/pacing electrode 270 is disposed over the lead body 257. The construction of this type of electrode structure, in particular the sensing/pacing electrode 271, 271 disposed circumferentially around a coil electrode 260, presents challenges in that electrical isolation between the coil and sensing/pacing electrodes is needed. A first method of construction that provides such electrical isolation involves cable break-outs, and is illustrated in FIGS. 7 and 8.

Figure 7:
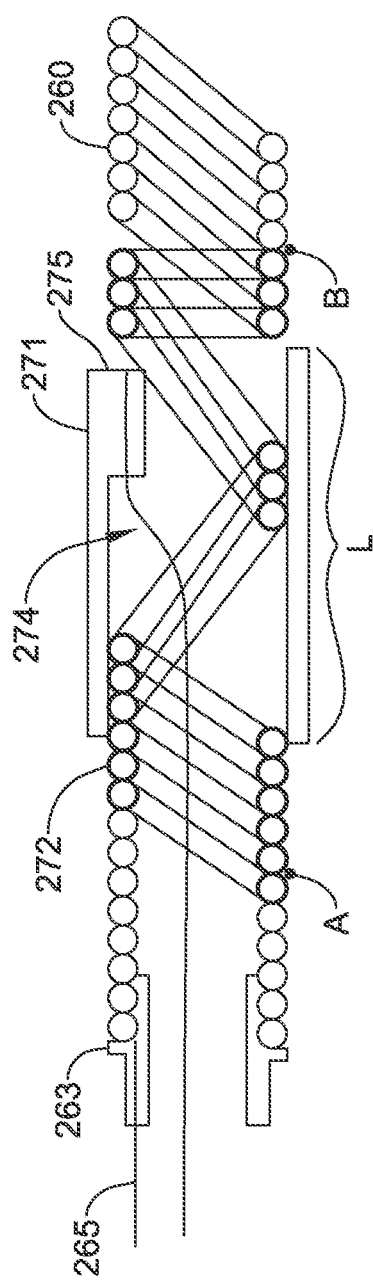
FIG. 7 is a partial cut-away view of another illustrative electrode structure.

FIG. 7 is a partial longitudinal cut-away illustration of the electrode structure 255 of FIG. 6, providing a close-up of the structure of ring sensing/pacing electrode 271 and coil electrode 260. The internal wall of the lead body 257 may be notched to accommodate the transition of the sensing/pacing cable 274 from a position within the central portion of the lead body to a position where the cable attaches to the underside of the sensing/pacing electrode 271.

A proximal end of the coil electrode 260 may be attached to a coupling element 263 to which a high voltage cable 265 is attached. The coil pitch may be increased at one or more locations along the longitudinal length L of the sensing/pacing electrode 271 to allow the sensing/pacing cable 274 to pass through the coil electrode 260, and to provide a space for the stake post 275 on the electrode 271 to which the sensing/pacing cable 274 is attached. The coil electrode 260 may be coated with insulating material 272 such as ETFE in the region from A to B as illustrated to maintain electrical isolation between the coil electrode 260 and the sensing/pacing electrode 271. In some examples, a tubing layer or sheath (not shown) may be added between the coil electrode 260 and the sensing/pacing electrode 271 for additional or alternative electrical isolation. In another example, an insulating element 172 may be provided by coating the inner surface of the ring electrode, as shown in FIG. 5.

Figure 8:
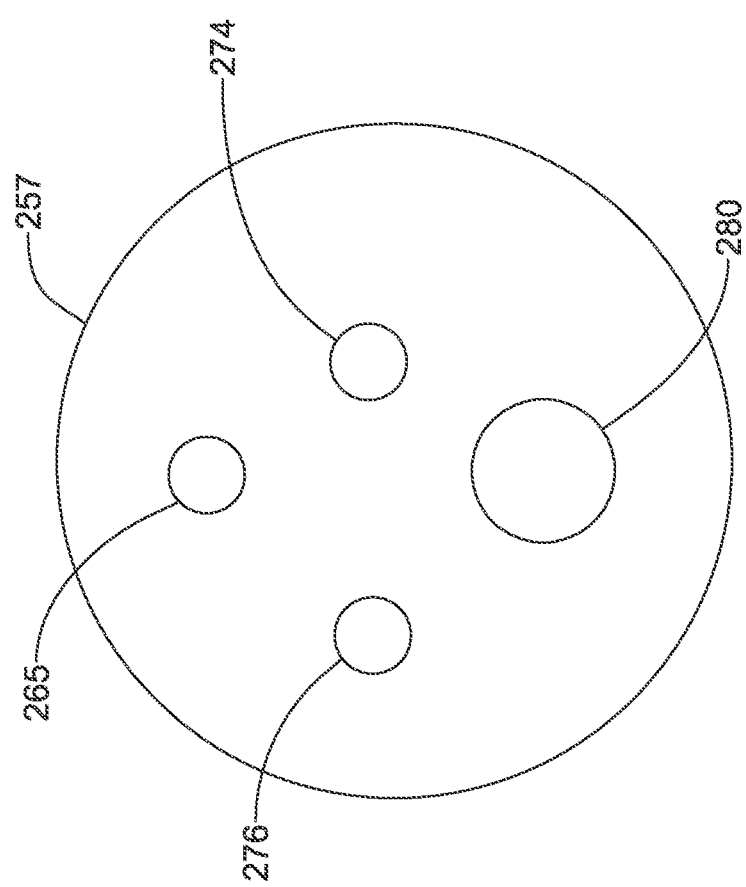
FIG. 8 is a radial cross-sectional view of another illustrative lead body.

FIG. 8 shows a cross-sectional view of a lead body 257, with the sensing/pacing electrodes and coil electrodes not shown for simplicity. The figure illustrates a possible orientation of the high voltage cable 265, two sensing/pacing cables 274, 276, and an internal lumen 280.

Figure 9:
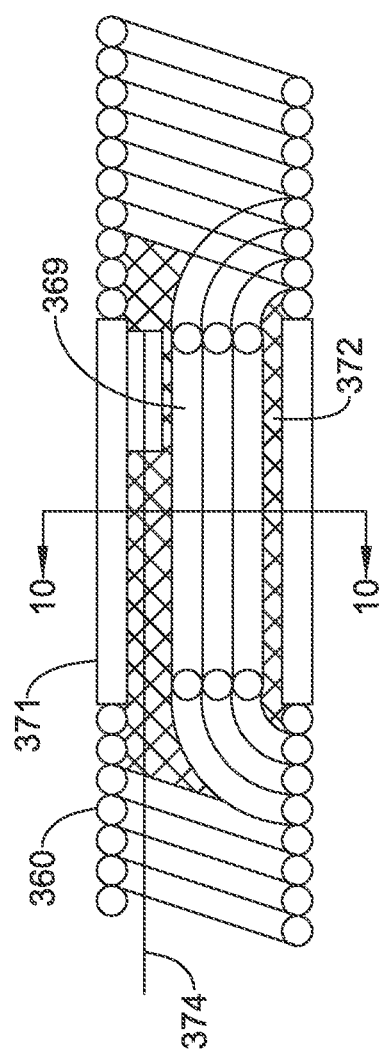
FIG. 9 is a partial cut-away view of another illustrative electrode structure.
Figure 10:
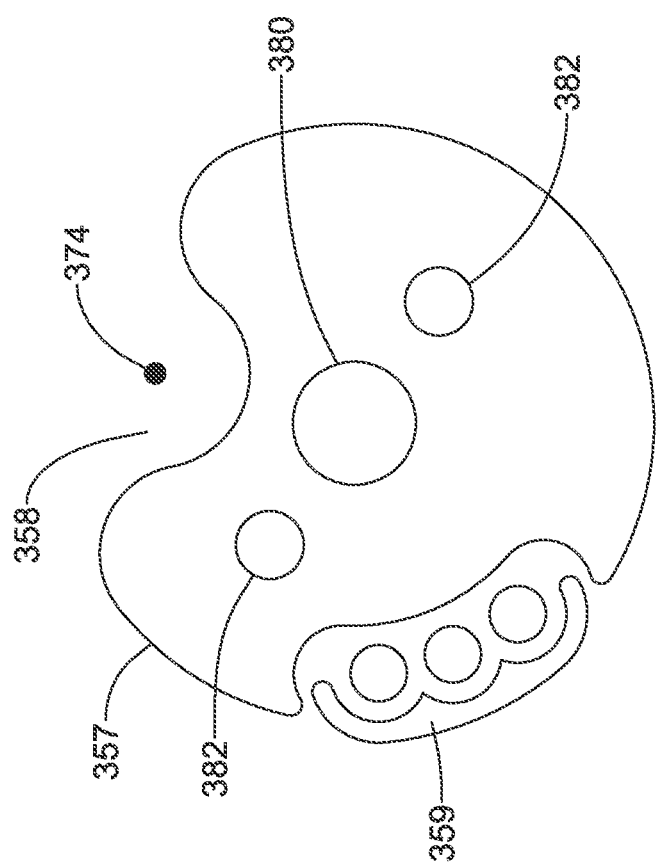
FIG. 10 is a radial cross-sectional view of another illustrative lead body.

A second method of construction to provide electrical isolation of the pace/sense electrode from the coil involves a preformed coil, as is illustrated in FIG. 9. The coil defibrillation electrode 360 includes a preformed region 369 that extends longitudinally through the sensing/pacing electrode 371. A gap between the sensing/pacing electrode 371 and the preformed region 369 may be back filled with insulation 372. In other examples, a pre-molded polymer insulating component may be added. The sensing/pacing cable 374 extends through the insulation 273 and attaches to the electrode 371. As seen in the cross-sectional view taken along line 10-10, FIG. 10 shows a lead body 357 with a cavity 358 for receiving the sensing/pacing cable 374, and a component 359 disposed over the preformed region 369 of the coil electrode to provide electrical isolation between the coil electrode and the sensing/pacing electrode 371, instead of the insulation 372. As shown in FIG. 10, a portion of the lead body may be cut away, indented, or flattened to receive the preformed region of the coil electrode and the associated component 359. FIG. 10 also shows an internal lumen 380 and additional sensing/pacing electrode cables 382.

Figure 11A:
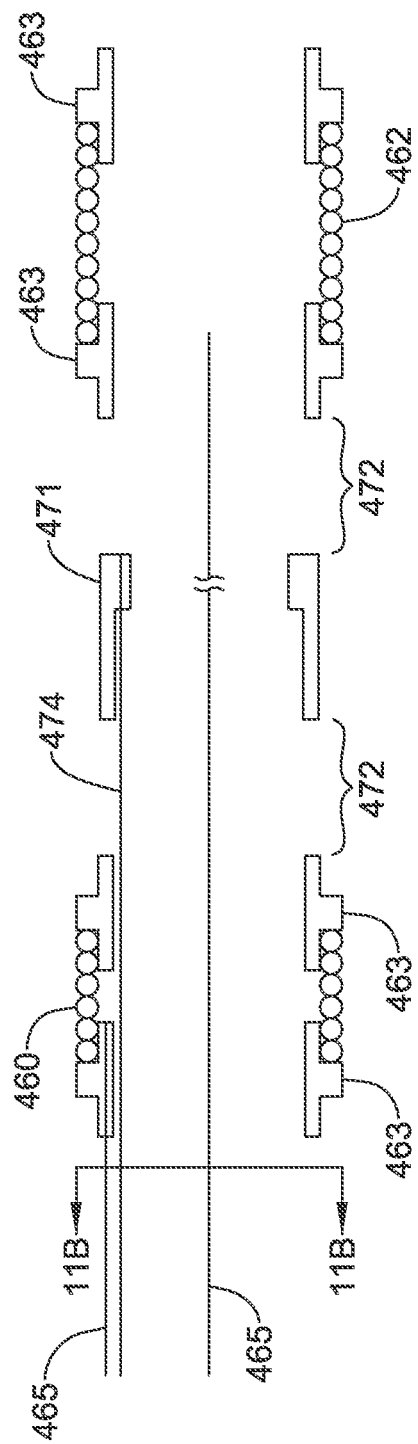
FIG. 11A is a partial cut-away view of another illustrative electrode structure.

A third method of construction to provide electrical isolation of the pace/sense electrode from the coil involves multiple coil segments, as is illustrated in FIGS. 11A and 11B. The sensing/pacing electrode 471 is disposed longitudinally between first and second coil electrodes 460, 462. The coil electrodes 460, 462 have coupling elements 463 on distal and proximal ends thereof. Each of the coil electrodes 460, 462 has a cable connector 465 extending proximally from the proximal coupling element 463. The sensing/pacing electrode 471 has a cable connector 474 extending proximally therefrom. The sensing/pacing electrode 471 is a paced apart longitudinally from the first and second coil electrodes 460, 462 by insulation elements 472. The insulation elements 472 may include regions of polymer tubing or other insulating material. One example of the orientation of the two high voltage cable connections 465 and the sensing/pacing electrode cable connector 474 within the lead body 457 is shown in FIG. 11B. The coil electrodes and sensing/pacing electrodes are not shown for simplicity. An internal lumen (not shown) may be included for receiving a delivery device, if desired.

Figure 12:
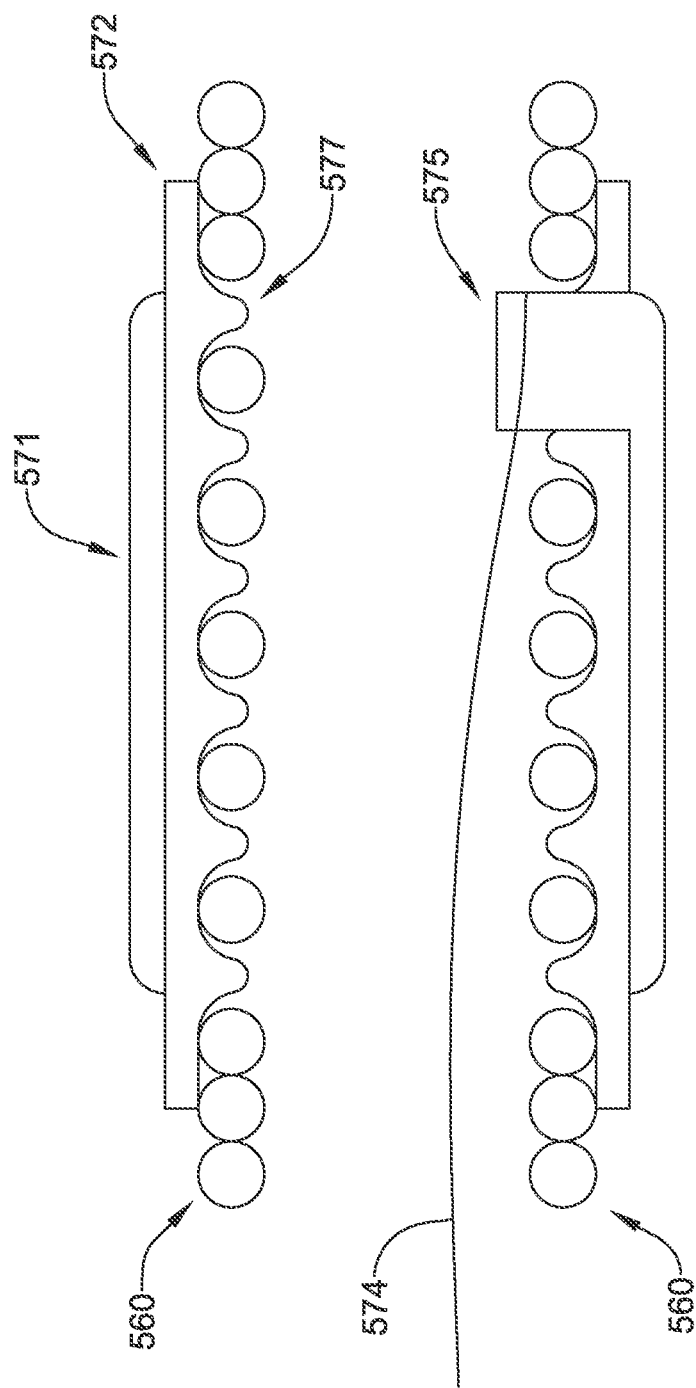
FIG. 12 is a partial cut-away view of another illustrative electrode structure.

FIG. 12 is a partial longitudinal cross-section of an electrode structure showing the use of an under molded threaded insulating element 572 to electrically isolate a sensing/pacing ring electrode 571 from a coil electrode 560. The insulating element 572 has a threaded inner surface 577 that has a threaded inner diameter configured to match the pitch and shape of the windings of the coil electrode 560. The insulating element 572 may be made of polyether ether ketone (PEEK) or other suitable electrically insulating material. The insulating element 572 may be formed as shown, for example by molding, or may be constructed on the lead by applying heat to shrink and reflow the insulating element 572 onto and around the coil electrode 560. The insulating element 572 may include an aperture for receiving the stake 575 of the sensing/pacing ring electrode 571 to which the sensing/pacing cable connector 574 is connected. The insulating element 572 may extend distally and proximally beyond the ends of the sensing/pacing ring electrode 571 to ensure complete electrical isolation between the sensing/pacing ring electrode 571 and the coil electrode 560.

Figure 13A:
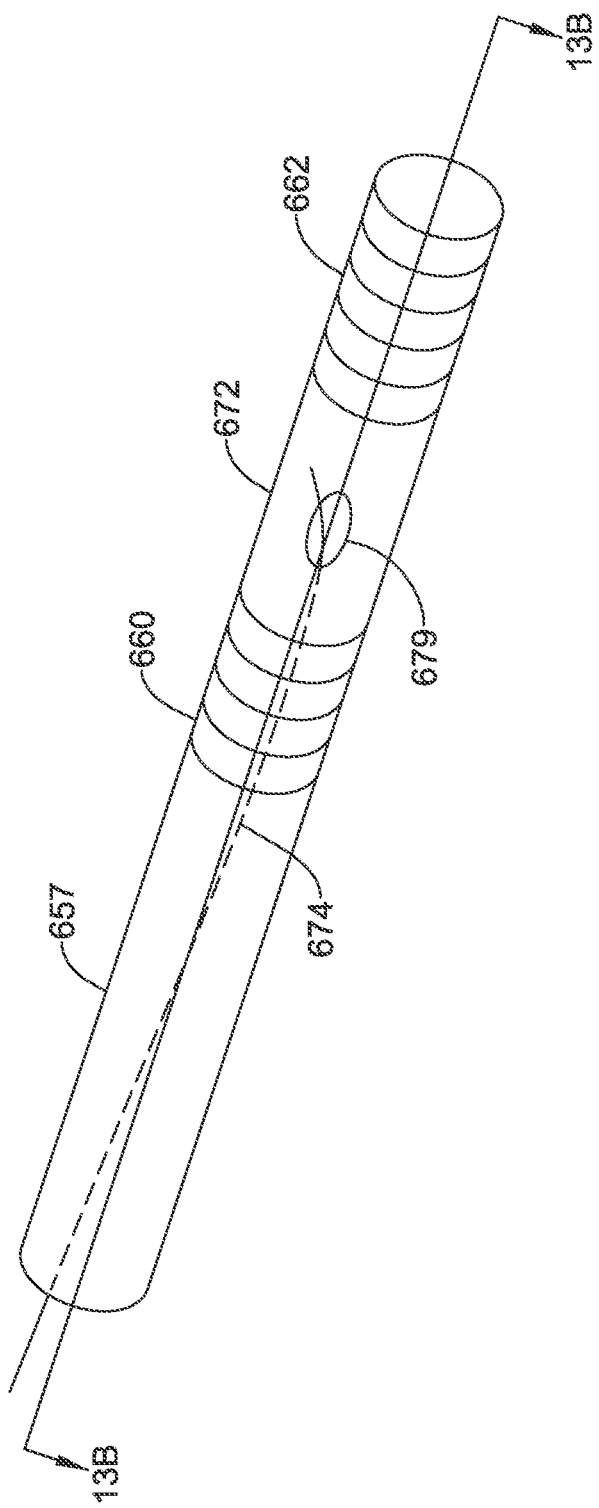
FIG. 13A is a perspective view of another illustrative electrode structure.

FIGS. 13A and 13B illustrate another example of insulating element 672 for electrically isolating the sensing/pacing electrode 671 from the coil electrode 660. FIG. 13A shows a perspective view of the lead body 657 with separate coil electrodes 660, 662 attached to proximal and distal ends of an insulating element 672. The sensing/pacing electrode 671 is not shown in FIG. 13A to illustrate the underlying insulating element 672. The insulating element 672 may have an aperture 679 therethrough for passage of the sensing/pacing electrode cable connector 674. As shown in FIG. 13B, a cross-section taken along line 13B-13B of FIG. 13A, the sensing/pacing electrode 671 is disposed over the insulating element 672 and attached to the cable connector 674. The lead body 657 is not shown in FIG. 13B to better illustrate the underlying elements. The insulating element 672 may have threading 677 on the inner surfaces of proximal and distal channels 678 which receive windings of the coil electrodes 660, 662. The insulating element 672 may be made of a hard plastic such as PEEK or a thermoplastic polyurethane (TPU) such as Tecothane™. Again the insulating element 672 may be made separately by molding, or may instead by formed onto the lead using heat shrink and reflow of an appropriate material.

Figure 14A:
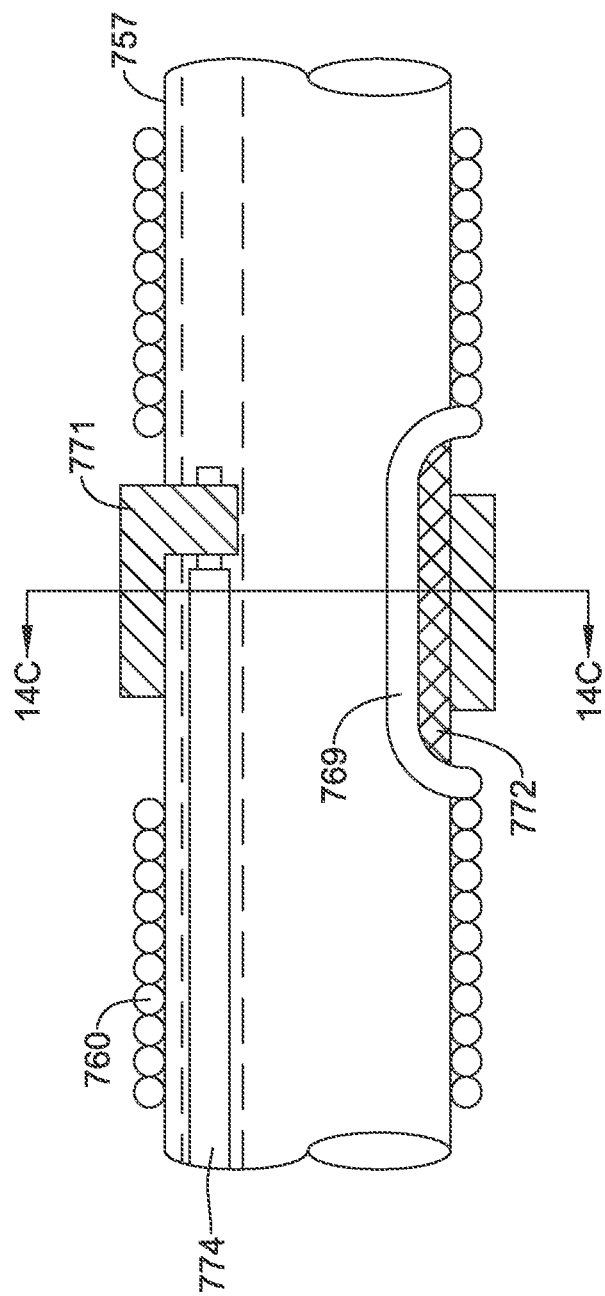
FIG. 14A is a partial longitudinal cross-sectional view of another illustrative electrode structure.
Figure 14B:
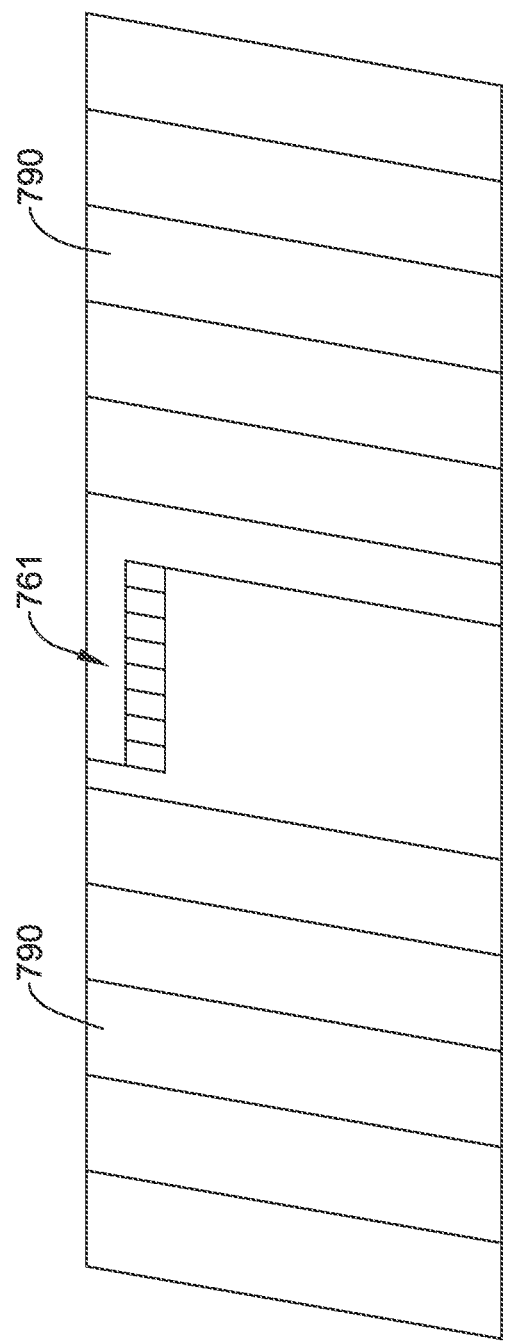
FIG. 14B is a side view of an illustrative coil electrode.
Figure 14C:
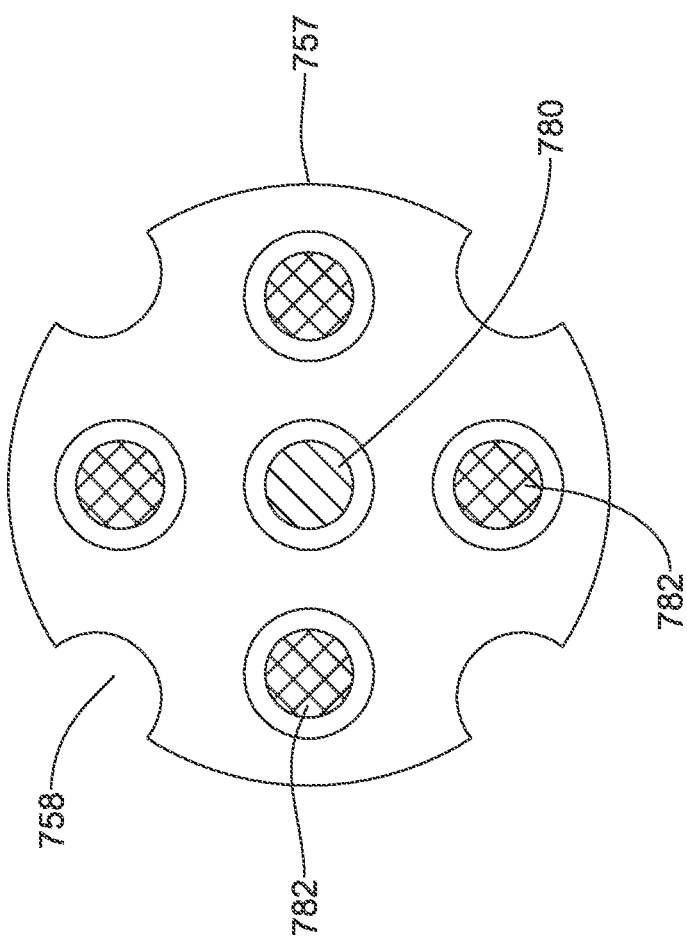
FIG. 14C is a radial cross-sectional view taken along line 14C-14C of FIG. 14A.

FIGS. 14A, 14B, and 14C illustrate a configuration in which the lead body 757 includes a coil electrode 760 with a straight portion 769 that is tunneled under the sensing/pacing electrode 771. The space between the straight portion 769 of the coil electrode 760 and the sensing/pacing electrode 771 may be filled with insulation 772. While the portion of the coil electrode 760 extending under the sensing/pacing electrode 771 is shown as a straight wire portion 769 in FIG. 14A, the portion of the coil electrode 760 may alternatively be a pigtail type segment, with a smaller radius coil 761 extending between larger radius coils 790, as shown in FIG. 14B. FIG. 14C is a cross-sectional view taken along line 14C-14C of FIG. 14A, but with the electrodes, cable connectors and insulating material removed for clarity. The lead body 757 may have one or more channels or recesses 758 extending longitudinally over a distance that corresponds to the distance the straight portion 769 extends between coiled portions, as shown in FIG. 14C. The recesses 758 may be spaced apart circumferentially as well as longitudinally along the lead body, providing for multiple instances where a portion of the coil electrode 760 tunnels under a sensing/pacing electrode 771. FIG. 14C also illustrates a device with four lumens 782 for carrying the cable connectors 774 attached to the sensing/pacing electrodes 771. An internal lumen 780 may also be provided for receiving a guide wire or other delivery device.

Figure 15A:
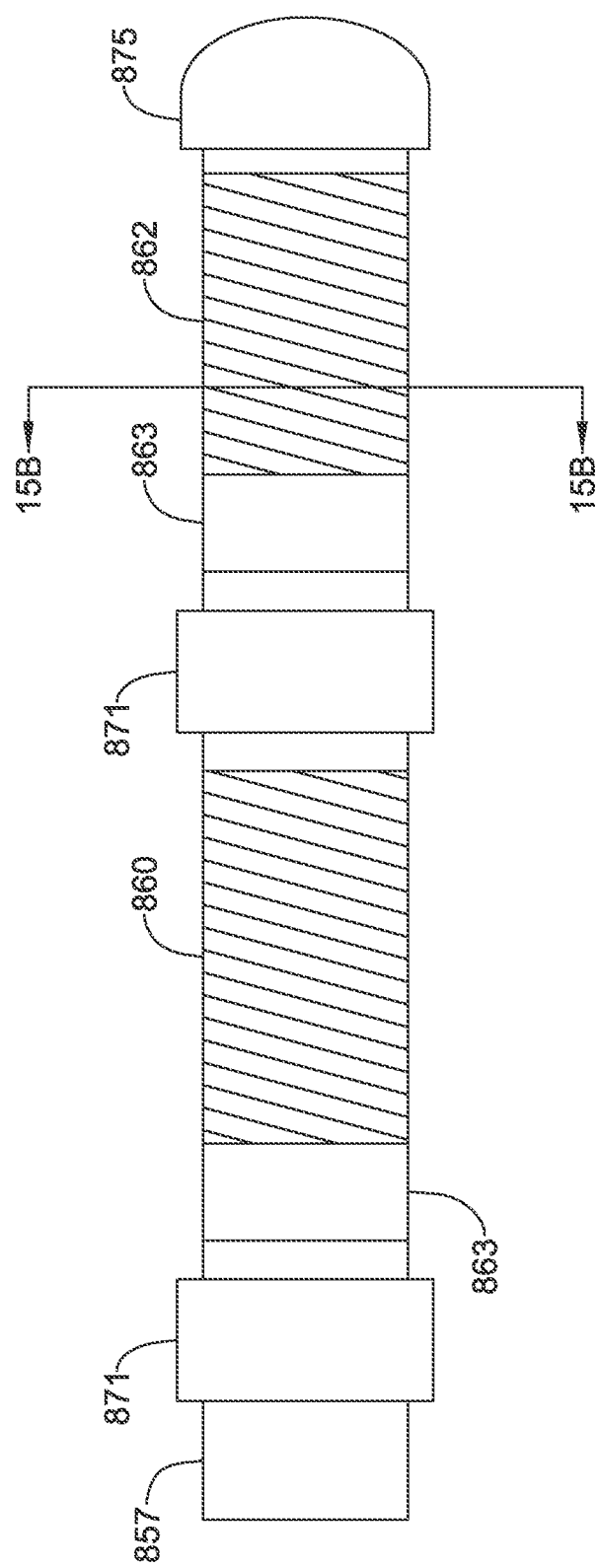
FIG. 15A is a side view of another illustrative electrode structure.
Figure 15B:
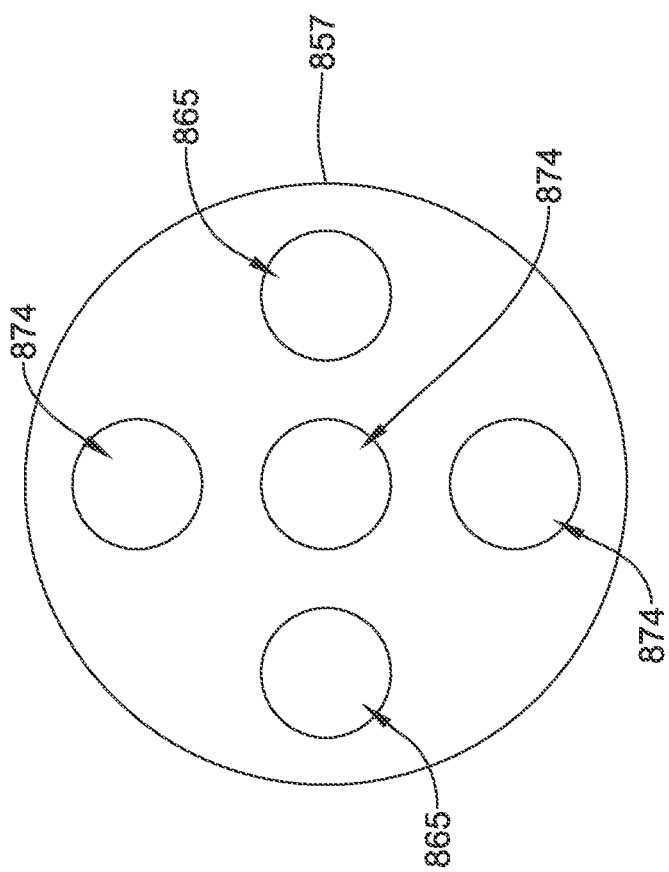
FIG. 15B is a radial cross-sectional view taken along lines 15B-15B of FIG. 15A.

An example of an interposed sensing/pacing and shocking coil electrode structure is illustrated in FIGS. 15A and 15B. FIG. 15A shows a lead body 857 that may have a tip electrode 875 with sensing/pacing ability, two sensing/pacing electrodes 871, and two separate shocking coil electrodes 860, 862. The coil electrodes 860, 862 each have coupling elements 863 to which the cable connectors (not shown) are attached. The sensing/pacing electrodes 871 may be ring electrodes. The coil electrodes 860, 862 are disposed between sensing/pacing electrodes 871, 875. In some examples, a portion of at least one end of the coil electrodes 860, 862 extends under a sensing/pacing electrode 871, 875. In one example, the distal end of the distal coil electrode may be disposed under the tip electrode 875, and the distal end of the proximal coil electrode 860 may be disposed under the distal sensing/pacing electrode 871. The coil electrodes 860, 862 and the tip electrode 875 or sensing/pacing electrode 871 may be electrically isolated using one of the insulating structures discussed above. The lead body 857 may have two lumens 865 for carrying the coil electrode cables, and may have any number of lumens 874 for carrying the sensing/pacing electrode cables and/or for receiving a delivery device. One example of a penta-lumen lead body 857 is illustrated in FIG. 15B, a cross-sectional view of the lead in FIG. 15A taken along line 15B-15B, with the electrodes removed for clarity.

Figure 16A:
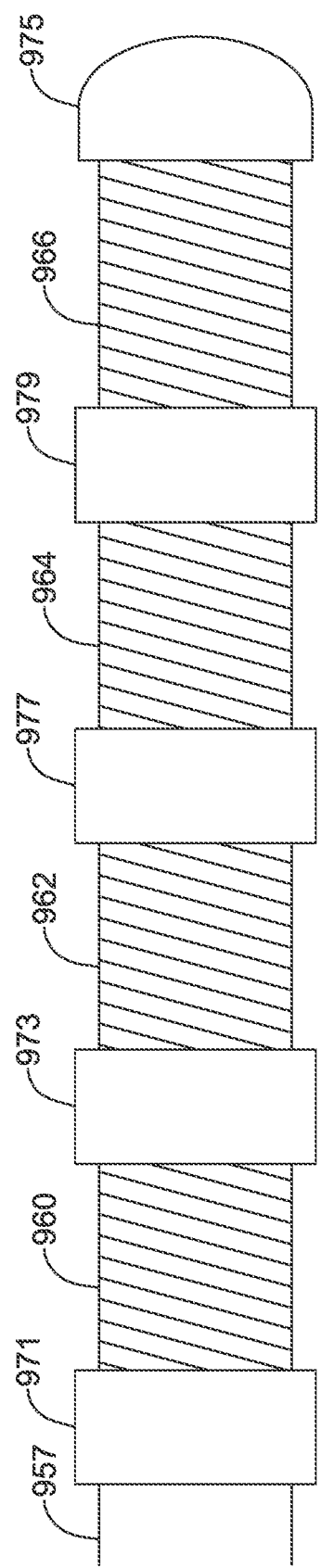
FIG. 16A is a side view of another illustrative electrode structure.
Figure 16B:
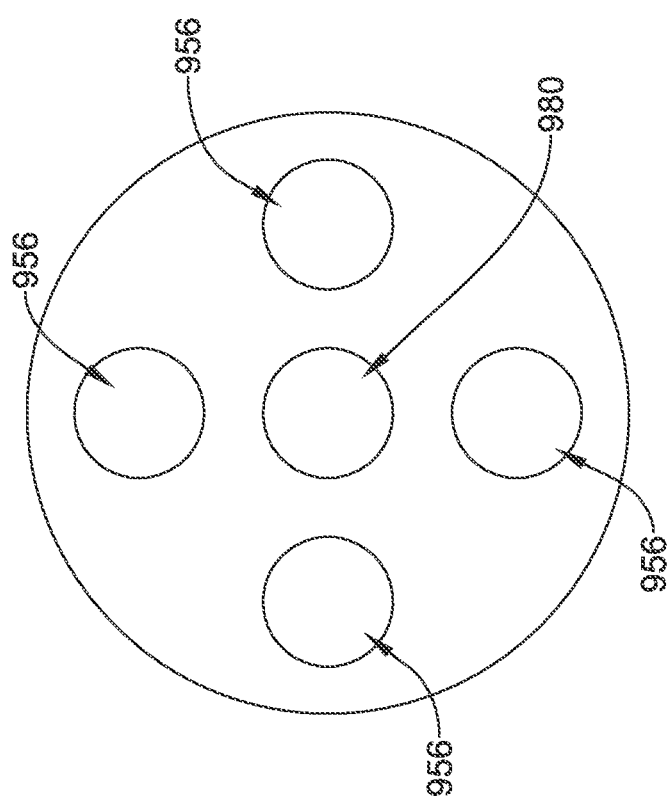
FIG. 16B is a radial cross-sectional view of another illustrative lead body.

FIGS. 16A and 16B illustrate an example of a mini shock coil lead body 957 with an integrated electrode structure including four coil electrodes 960, 962, 964, 966, four sensing/pacing electrodes 971, 973, 977, 979, and a tip electrode 975. The coil electrodes and the sensing/pacing electrodes may be electrically isolated from each other using any of the methods and structures described above. Further, the coil electrodes 960, 962, 964, 966 may extending under one or more of the sensing/pacing electrodes 971, 973, 977, 979 or the tip electrode 975, as described above. In another example, the coil electrode is a single electrode extending between and under all of the sensing/pacing electrodes. FIG. 16B illustrates an example of the orientation of lumens for receiving the electrode cables. FIG. 16B is a cross-sectional view of a lead that may include electrodes as in FIG. 16A. The electrodes are not shown in FIG. 16B for clarity. The center lumen 980 may receive a cable from the tip electrode 975 and the four surrounding lumens 956 may receive integrated sensing/pacing and shock coil cables.

Figure 17A:
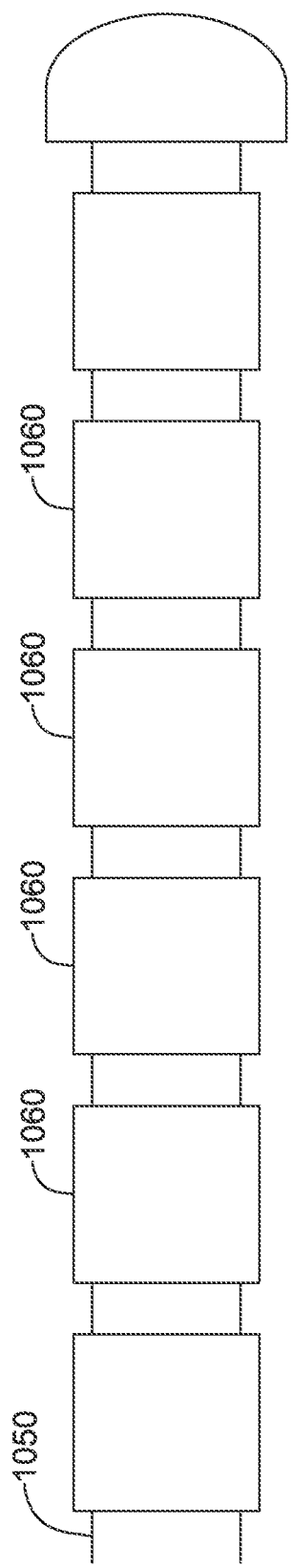
FIG. 17A is a side view of another illustrative electrode structure.

FIGS. 17A and 17B illustrate an example lead body 1050 in which multiple electrodes 1060 provide shocking energy. In some examples, all of the electrodes 1060 may be engaged to deliver shocking energy. The electrodes may have common conductors so the risk of shorting is minimal. A low voltage sense/pace signal may be used so that minimal insulation between the electrodes is needed. FIG. 17B illustrates one example of an orientation for electrode conductors in a lead body such as lead body 1050. FIG. 17B does not show the electrodes for clarity. The lead body 1050 may have as many lumens 1040 as needed for receiving the conductors from the electrodes 1060. In the example illustrated, the cables from the eight electrodes 1060 may be received in eight lumens 1040 surrounding a central lumen 1080 for receiving a delivery device.

It will be understood that the internal lumens shown in the above examples are optional, depending on the method of insertion. In some methods, the internal lumens may receive a guide wire or stylus. In other methods, no internal lumen is present, for example, when the lead is implanted within a sheath, or by use of a pulling method such as disclosed in U.S. Pat. No. 8,157,813, the disclosure of which is incorporated herein by reference.

FIGS. 18-23 illustrate various lead designs with attachment structures. These lead designs may be applied to any of the leads and electrode structures described above. These leads may be manufactured of any suitable material and by any suitable manner. For example, numerous polymers are known for lead manufacture. Internal longitudinal or lateral support members, such as braids, core wires, etc. may be provided. Extrusion or molding may be used. Internal conductors may be formed of any suitable material (stainless steel, titanium, gold, silver, or any other conductive material may be used) and may take any suitable form, such as simple wires, coated wires, braided or wound wires, drawn wires, and/or drawn filled tubes, or other structures. The leads may include on all or a portion thereof various coatings such as an anti-microbial coating to reduce the likelihood, severity, and/or progression of infection. Some illustrative lists for such design details follow later in the disclosure.

Figure 18:
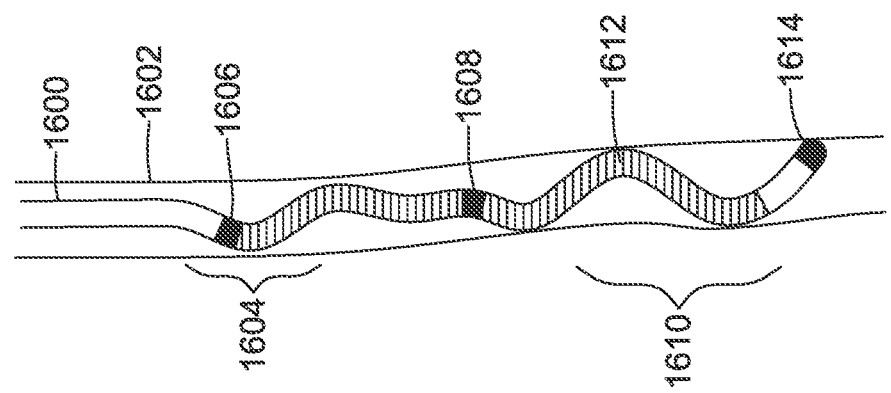

FIG. 18 shows an illustrative lead structure. A lead 1600 is shown within a blood vessel 1602, which may be an ITV. The lead may include sensing/pacing ring electrodes illustrated at 1606, 1608, and a tip electrode 1614, as well as a continuous coil electrode at 1612. Regions of curvature area shown at 1604, and at 1610. A single curvature may be provided instead. The curvature may be two-dimensional or three-dimensional. A two dimensional curvature may take the form, generally, of a zig-zag design, for example. Several embodiments may use a three dimensional curvature such as a pigtail or helix, for example.

In FIG. 18, the curvature may be assumed by the lead in several ways. In an example, the lead includes a shape memory material and is generally straight and flexible until implanted in the body; after a few minutes to warm up, the shape memory material assumes the shape shown. In another example, a stylet is placed inside the lead during implantation to retain a generally straight shape, and the lead assumes the curved shape shown when the stylet is removed. In another example, an outer sheath is used to retain the lead until it is implanted with removal of the outer sheath allowing the lead to assume a desired shape. Combinations may be used as well; for example, a lead may include a shape memory portion or material or support structure, and may be implanted with the aid of a stylet and outer sheath to retain a low profile for implantation and then, once released by removal of the stylet and sheath, the shape memory material exerts forces to assume the shapes shown. Though not shown, curvature may be used for secure placement of any of the leads shown in FIGS. 19-24, if desired.

Figure 19:
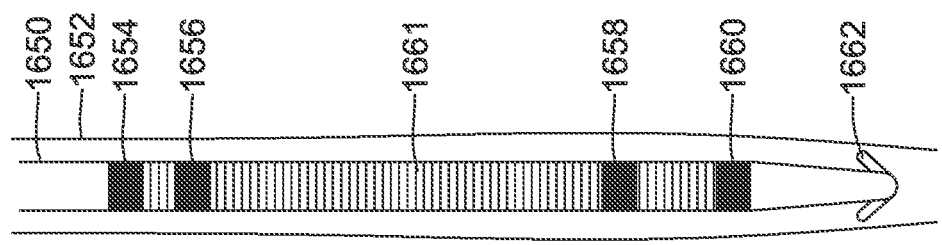

FIG. 19 shows another example of a lead with an attachment structure. Here, a lead 1650 is shown inside a blood vessel 1652, which may be the ITV. First and second ring electrodes are shown at 1654, 1656, and third and fourth ring electrodes are shown at 1658, 1660. A continuous coil electrode 1661 extends under all four ring electrodes 1654, 1656, 1658, 1660. This structure with portions of the coil electrode 1661 disposed at the same location as the ring electrodes 1654, 1656, 1658, 1660 would allow sensing and pacing directly over the heart. Tines for fixation are shown at 1662. The ring electrodes may be placed such that if the tines 1662 are superior relative to the rest of the lead, electrodes 1658, 1660 would be level with the atria, and electrodes 1654, 1656 would be level with the ventricles. This may facilitate separate atrial and ventricular sensing and/or pacing channels.

Figure 20:
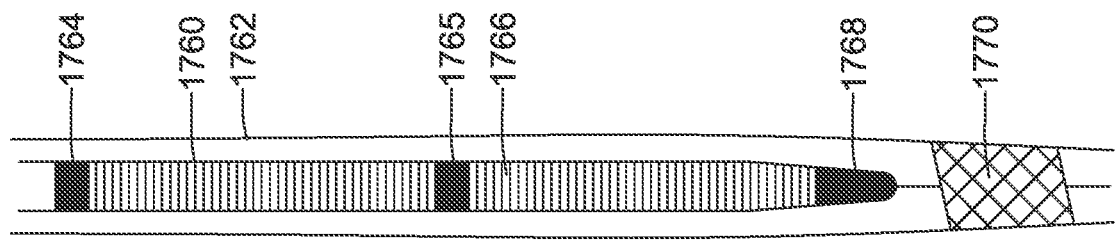
FIGS. 18-23 illustrate various lead designs.

FIG. 20 shows another example. The lead 1760 shown inside a blood vessel 1762 which may be a ITV, and with a proximal ring electrode 1764, continuous coil electrode 1766, and distal tip electrode 1768. However, now, an expandable member, such as a stent 1770 is shown distal to the distal tip electrode 1768. For example, a self-expanding stent 1770 may be provided and carried within the distal tip electrode 1768 until a desired position is reached for the stent 1770. Such positioning may be determined using, for example, fluoroscopy. The proximal end of the lead may include a release mechanism, such as a control wire that can be advanced relative to the lead body, to push the stent 1770 beyond the distal tip electrode 1768 where it can then release. Self-expanding stents are well known in the art and may include, for example, spring-like structures. The stent 1770 may include coatings designed to prevent thrombus from forming thereon and/or to encourage angiogenesis to best engage the venous wall. For removal, the connection to the stent 1770 may be cut, for example, to leave the stent 1770 in place as the rest of the lead is removed. Optionally the stent may be later removed using, for example, a stent retriever.

Figure 21:
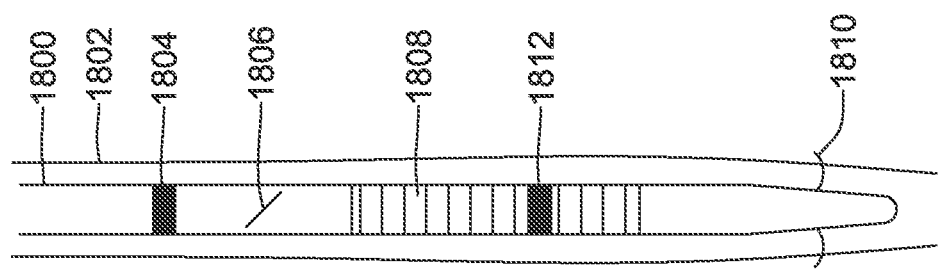

FIG. 21 shows another example. Here, a lead 1800 is shown in a blood vessel 1802 which may be an ITV. A proximal ring electrode is shown at 1804. Distal of the proximal ring electrode (though any suitable location, more proximal or more distal, may be chosen), a side-engaging member is shown at 1806. For example, engaging member 1806 may be an arm, coil, hook, or tine that expands outward when actuated from the proximal end of the lead. Once the lead is in a desired position, engaging member 1806 may be actuated to secure the lead in place.

The lead 1800 is also shown with a coil electrode at 1808 and a distal ring electrode 1812 disposed over the coil electrode 1808. Finally, at the distal tip of the lead, a plurality of hooks are shown for engaging the walls of the blood vessel 1802. The engaging member 1806 or hooks 1810 may be coated as desired for anti-thrombogenic or pro-angiogenic reasons, for example.

Figure 22:
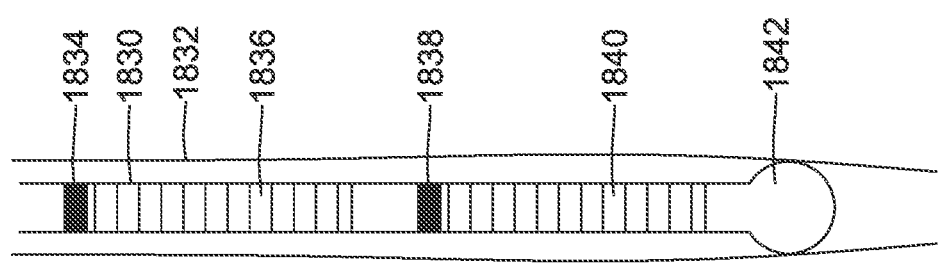

FIG. 22 shows another example. Here, a lead 1830 is shown inside of a blood vessel 1832 which may be an ITV. A plurality of electrodes are shown including a first ring electrode 1834, first coil electrode 1836, second ring electrode 1838, and second coil electrode 1840. At the distal end of the lead is an expandable member, such as a balloon 1842, which may be inflated to secure the lead in place. It should be noted that the ITV is a blood vessel which, if occluded, will not necessarily cause harm to the patient as contralateral accommodation occurs readily. The balloon 1842 may be expanded using inflation pressure, for example. A compliant or non-complaint material may be used the balloon. Rather than a balloon, an expandable sponge-type member that increases in volume once sufficiently wetted may be used instead.

Figure 23:
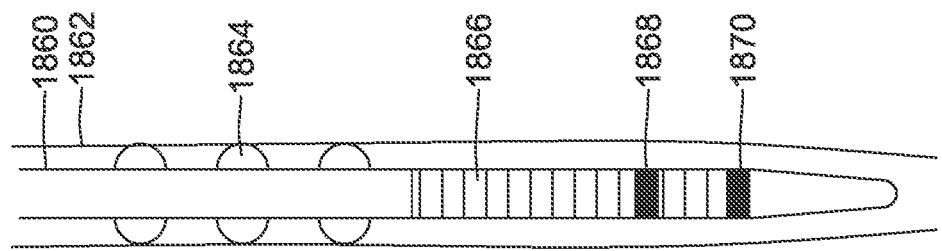

FIG. 23 shows another example. In this example, the lead 1860 is shown in a blood vessel 1862 which may be an ITV. This example includes a plurality of lobes 1864 which hold the lead 1860 in place inside the blood vessel 1862. For example, the lobes may self-expand on removal of an outer delivery sheath or catheter, or the lobes may be expanded by movement of an outer shell of the lead relative to an inner shell. A coil electrode is shown at 1866 and ring electrodes are shown at 1868, 1870.

The examples of attachment structures in FIGS. 18-23 are merely illustrative. Some examples may omit any fixation on the portion of the lead that extends into the blood vessel, and may instead rely on fixation using a suture sleeve subcutaneously placed as shown in certain of the above examples. In some examples, a relatively stiff lead may be used, as repeated flexion is not necessary when implanted in the ITV in the same manner as is the case inside the heart. A stiff lead is believed to be less likely to migrate. The placement of the coil and ring electrodes along the lead in the examples of FIGS. 18-23 may be altered and the orientation of the coil and ring electrodes may be as described in any of the above examples, including ring electrodes disposed directly on the coil as illustrated in FIGS. 5, 8, 9, 12, 13B, 14A, and ring electrodes spaced apart longitudinally from separate coil electrodes, as illustrated in FIG. 11A.

In some examples, the structures shown in FIGS. 18-23 may be adapted for subcutaneous placement using hooks, tines, curvature or the like. In still further examples, a suture hole may be placed at the distal tip of the lead as shown in U.S. Pat. No. 8,483,841. In the example illustrated in FIG. 5, the insulation 172 does not extend longitudinally beyond the ring electrodes 171, 173. In some examples, the insulation between a ring electrode and the coil electrode may extend longitudinally beyond the ring electrode, for a span a distance in the range of, for example, 0-50 mm, 0-5 mm, 5-15 mm, 15-30 mm, 30-50 mm on each side of the ring electrode.

In any of the above examples, additional lead placement may take place. For example, an additional lead may be placed subcutaneously, within the heart, or in a different blood vessel such as the azygos vein. Additional device placement may occur as well, including, for example, the placement of a leadless cardiac pacemaker in one or more chambers of the heart.

Prior transvenous systems would typically deliver up to 35 Joules of energy at most, with storage of up to 40 Joules of energy, using peak voltages in the range of up to nearly 1000 volts. The S-ICD System can deliver up to 80 Joules of energy, with 65 Joules often used for in-clinic system testing, with a peak voltage in the range of 1500 volts. The ITV location may facilitate energy levels similar to those of traditional transvenous systems (5-35 Joules, approximately), or may be somewhat higher (5 to about 50 joules, for example), or may still be higher (10 to about 60 joules, for example). Pacing thresholds may also be closer to those for traditional transvenous systems than the more recent S-ICD System.

In an example, pacing testing operation may include determining which, if any, available pacing vectors are effective to provide pacing capture. If desired, parameters may be tested as well to determine and optimize settings for delivery of cardiac resynchronization therapy. This may include testing of pacing thresholds to optimize energy usage and delivery, as well as checking that adverse secondary effects, such as patient sensation of the delivered pacing or inadvertent stimulation of the phrenic nerve, diaphragm or skeletal muscles are avoided.

Some embodiments of the present invention may take the form of an implantation tool set configured for use in implanting a cardiac device, such as a lead, into an ITV. Some such embodiments may include an introducer sheath. Some such embodiments may include a guide catheter. Some such embodiments may include a guidewire. Some such embodiments may further include a tool set for performing a Seldinger technique to access a blood vessel percutaneously.

Some embodiments of the present invention take the form of an implantable cardiac stimulus device comprising a lead and an implantable canister for coupling to the lead, the implantable canister housing operational circuitry configured to deliver output therapy in the form of at least one of bradycardia pacing, anti-tachycardia pacing, cardiac resynchronization therapy, or defibrillation, using a lead implanted in an ITV and a canister implanted in a patient.

As used herein, a coil electrode may be a helically wound element, filament, or strand. The filament forming the coil may have a generally round or a generally flat (e.g. rectangular) cross-sectional shape, as desired. However, other cross-sectional shapes may be used. The coil electrode may have a closed pitch, or in other words, adjacent windings may contact one another. Alternatively, the coil electrode may have an open pitch such that adjacent windings are spaced a distance from one another. The pitch may be uniform or varied along a length of the coil electrode. A varied pitch may be gradual tapered changes in pitch or abrupt or step-wise changes in pitch.

A coil electrode may have a length L measured in the longitudinal direction that is generally larger than a width W measured in the radial direction. Round, oval or flattened coil electrodes may be used. Coil electrodes may have a length in the range of one to ten centimeters. In an example, a coil having a six or eight centimeter length may be used. In another example, a lead may have two four centimeter coils. Coils and leads may be in the range of four to ten French, or larger or smaller, in outer profile.

Coils and leads may be coated. For example, a thin permeable membrane may be positioned over a shock coil or other electrode and/or other portions of the lead to inhibit or to promote tissue ingrowth. Coatings, such as, but not limited to expanded polytetrafluoroethylene (ePTFE) may also be applied to the coil and/or lead to facilitate extraction and/or to reduce tissue ingrowth. In some embodiments, one or more of the electrodes, whether coils, rings, or segmented electrodes, include a high capacitive coating such as, but not limited to iridium oxide (IrOx), titanium nitride (TiN), or other "fractal" coatings which may be used, for example, to improve electrical performance. Steroidal and antimicrobial coatings may be provided as well.

The various components of the devices/systems disclosed herein may include a metal, metal alloy, polymer, a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers for use in the leads discussed above may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like.

In at least some embodiments, portions or all of the accessory devices and their related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the accessory devices and their related components to achieve the same result.

Any guidewire, introducer sheath, and/or guide catheter design suitable for medical interventions may be used for accessing the venous structures discussed herein.

The implantable systems shown above may include an implantable pulse generator (IPG) adapted for use in a cardiac therapy system. The IPG may include a hermetically sealed canister that houses the operational circuitry of the system. The operational circuitry may include various elements such as a battery, and one or more of low-power and high-power circuitry. Low-power circuitry may be used for sensing cardiac signals including filtering, amplifying and digitizing sensed data. Low-power circuitry may also be used for certain cardiac therapy outputs such as pacing output, as well as an annunciator, such as a beeper or buzzer, telemetry circuitry for RF, conducted or inductive communication (or, alternatively, infrared, sonic and/or cellular) for use with a non-implanted programmer or communicator. The operational circuitry may also comprise memory and logic circuitry that will typically couple with one another via a control module which may include a controller or processor. High power circuitry such as high power capacitors, a charger, and an output circuit such as an H-bridge having high power switches may also be provided for delivering, for example, defibrillation therapy. Other circuitry and actuators may be included such as an accelerometer or thermistor to detected changes in patient position or temperature for various purposes, output actuators for delivering a therapeutic substance such as a drug, insulin or insulin replacement, for example.

Some illustrative examples for hardware, leads and the like for implantable defibrillators may be found in commercially available systems such as the Boston Scientific Teligen™ ICD and Emblem S-ICD™ System, Medtronic Concerto™ and Virtuoso™ systems, and St. Jude Medical Promote™ RF and Current™ RF systems, as well as the leads provided for use with such systems.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable lead for use with an implantable cardiac stimulus device, the lead comprising:
   a lead body having a longitudinal axis extending between a proximal end and a distal end, wherein the proximal end is adapted for coupling to the implantable cardiac stimulus device;
   a cable conductor extending through the lead body; and
   an electrode structure disposed adjacent the distal end of the lead body, the electrode structure including a plurality of electrodes that are electrically isolated from one another, wherein the plurality of electrodes includes a first electrode and a second electrode, wherein at least a portion of the first electrode and at least a portion of the second electrode overlap one another at a longitudinal location on the lead;

wherein the first electrode is a coil electrode having a plurality of windings, the windings defining spaces longitudinally therebetween, and the second electrode is a ring electrode coupled to the cable conductor extending through the lead body, wherein the ring electrode is coupled to the cable conductor through a space between the windings of the coil electrode.

2. The implantable lead of claim 1, wherein the coil electrode is a single continuous coil and has a first section and a second section spaced apart longitudinally from the first section, and at least a portion of the ring electrode is disposed between the first and second sections of the coil electrode.

3. The implantable lead of claim 2, further comprising insulation disposed between the first and second electrodes, wherein the first and second electrodes are separated radially by a space, wherein the insulation includes an insulating element that fills the space.

4. The implantable lead of claim 3, wherein the coil electrode includes a preformed region between the first and second sections, the preformed region extending longitudinally through the ring electrode, wherein the insulation is disposed between the preformed region of the coil and the ring electrode.

5. The implantable lead of claim 4, wherein the lead body includes one or more recesses on an outer surface thereof, each recess configured to receive the preformed region of the coil electrode.

6. The implantable lead of claim 3, wherein the insulating element includes a threaded inner surface configured to receive the coil windings of the coil electrode.

7. The implantable lead of claim 3, wherein the insulating element includes an aperture therethrough for receiving the cable conductor coupled to the ring electrode.

8. The implantable lead of claim 1, wherein the coil electrode is a high voltage shocking electrode and the ring electrode is a sensing and/or pacing electrode.

9. The implantable lead of claim 1, wherein the plurality of electrodes includes three to eight electrodes.

10. The implantable lead of claim 1, further comprising insulation disposed between the first and second electrodes.

11. The implantable lead of claim 10, wherein the insulation includes an insulating coating disposed on an inner surface of the ring electrode or on a portion of the coil electrode that contacts the ring electrode, or both.

12. The implantable lead of claim 10, wherein the insulation includes an insulating element disposed on an inner surface of the ring electrode, wherein the insulating element contacts the coil electrode to insulate the first electrode from the second electrode.

13. The implantable lead of claim 10, wherein the plurality of electrodes further comprises a second coil electrode, wherein the insulation includes an insulating element including proximal and distal channels configured to receive a distal end of the coil electrode and a proximal end of the second coil electrode.

14. The implantable lead of claim 1, wherein the space is defined by a region of the coil windings having an increased pitch compared to regions of the coil distal and proximal of the ring electrode.

15. The implantable lead of claim 14, wherein the region of the coil windings having an increased pitch is disposed under the ring electrode.

16. The implantable lead of claim 1, further comprising a distal terminal electrode.

17. The implantable lead of claim 1, wherein the ring electrode is a first sensing/pacing ring electrode and the cable conductor is a first cable conductor coupled to the first sensing/pacing ring electrode, wherein:
the lead further comprises a second cable conductor and a third cable conductor;
the lead body defines a first lumen and a second lumen;
the plurality of electrodes further includes a second sensing/pacing ring electrode coupled to the second cable conductor;
the first and second cable conductors extend proximally in a co-radial coil through the first lumen in the lead body; and
the third cable conductor is attached to the coil electrode and extends proximally through the second lumen in the lead body.

18. An implantable lead for use with an implantable cardiac stimulus device, the lead comprising:
a lead body having a longitudinal axis extending between a proximal end and a distal end, wherein the proximal end is adapted for coupling to the implantable cardiac stimulus device;
a cable conductor extending through the lead body;
a coupling member;
an electrode structure disposed adjacent the distal end of the lead body, the electrode structure including at least one coil electrode having a plurality of windings, the windings defining spaces longitudinally therebetween, and at least one ring electrode coupled to the cable conductor by the coupling member, wherein at least a portion of the coil electrode and at least a portion of the ring electrode overlap one another at a longitudinal location on the lead, wherein one or more of the ring electrode, the cable conductor, and the coupling member extends radially through a space between the windings of the coil electrode; and
insulation disposed on an inner surface of the ring electrode or on a portion of the coil electrode that contacts the ring electrode, or both.

19. An implantable cardiac stimulus system, comprising:
an implantable cardiac stimulus device;
a lead body connectable to the implantable cardiac stimulus device, the lead body having a longitudinal axis extending between a proximal end and a distal end, wherein the proximal end is adapted for coupling to the implantable cardiac stimulus device;
at least first and second cable conductors extending through the lead body; a connector and
an electrode structure disposed adjacent the distal end of the lead body, the electrode structure including at least first and second electrodes that are electrically isolated from one another, wherein at least a portion of the first electrode and at least a portion of the second electrode overlap one another at a longitudinal location on the lead;
wherein the first electrode is a single continuous coil electrode comprising windings about the lead body with spaces therebetween, the continuous coil electrode having a first section and a second section spaced apart longitudinally from the first section, wherein at least a portion of the second electrode is disposed between the first and second sections of the coil electrode, the first electrode being coupled at least to the first cable conductor, and the second electrode being coupled to the second cable conductor by the connector extending through one of the spaces between the windings.

* * * * *